United States Patent
Forim et al.

(10) Patent No.: US 9,668,473 B2
(45) Date of Patent: Jun. 6, 2017

(54) **PROCESS FOR OBTAINING BIOPOLYMERIC NANOPARTICLES CONTAINING *AZADIRACHTA INDICA* A. JUSS. (NEEM.) OIL AND EXTRACTS, BIOPOLYMERIC NANOPARTICLES, AND POWDER MICROPARTICLES**

(71) Applicant: FUNDAÇÃO UNIVERSIDADE FEDERAL DE SÃO CARLOS, São Carlos (BR)

(72) Inventors: Moacir Rossi Forim, São Carlos (BR); Maria Fátima das Graças Fernandes Da Silva, São Carlos (BR); João Batista Fernandes, São Carlos (BR); Paulo Cesar Vieira, São Carlos (BR)

(73) Assignee: FUNDACAO UNIVERSIDADE FEDERAL DE SAO CARLOS, Sao Carlos (BR)

( * ) Notice: Subject to any disclaimer, the term of this patent is extended or adjusted under 35 U.S.C. 154(b) by 0 days.

(21) Appl. No.: 14/762,262

(22) PCT Filed: Jan. 23, 2014

(86) PCT No.: PCT/BR2014/000044
§ 371 (c)(1),
(2) Date: Jul. 21, 2015

(87) PCT Pub. No.: WO2014/113860
PCT Pub. Date: Jul. 31, 2014

(65) Prior Publication Data
US 2015/0320036 A1    Nov. 12, 2015

(30) Foreign Application Priority Data

Jan. 25, 2013   (BR) .......................... 102013021210

(51) Int. Cl.
| | | |
|---|---|---|
| *A01N 25/28* | (2006.01) | |
| *A61K 9/14* | (2006.01) | |
| *A01N 65/26* | (2009.01) | |
| *A01N 43/90* | (2006.01) | |
| *A01N 25/12* | (2006.01) | |

(52) U.S. Cl.
CPC ............. *A01N 25/28* (2013.01); *A01N 25/12* (2013.01); *A01N 43/90* (2013.01); *A01N 65/26* (2013.01); *A61K 9/14* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | |
|---|---|---|
| 5,009,886 A | 4/1991 | Ahmad et al. |
| 5,411,736 A | 5/1995 | Locke et al. |
| 5,420,318 A | 5/1995 | Lidert et al. |
| H1541 H * | 6/1996 | Holla ............... A01N 65/26 424/761 |
| 5,643,351 A | 7/1997 | Lew et al. |
| 5,695,763 A | 12/1997 | Kleeberg |
| 5,736,145 A | 4/1998 | Murali |
| 5,827,521 A | 10/1998 | Moorty et al. |
| 5,856,526 A | 1/1999 | Sankaram et al. |
| 6,193,974 B1 | 2/2001 | Murali |
| 6,340,484 B1 | 1/2002 | Damaria et al. |
| 6,596,292 B2 | 7/2003 | Nishi |
| 6,635,757 B1 | 10/2003 | Kumble et al. |
| 6,667,277 B2 | 12/2003 | Hartmann et al. |
| 6,703,034 B2 | 3/2004 | Parmar et al. |
| 6,733,802 B1 | 5/2004 | Moorty et al. |
| 6,811,790 B1 | 11/2004 | Damaria et al. |
| 7,538,079 B2 | 5/2009 | Warr et al. |
| 7,655,597 B1 | 2/2010 | Sanders |
| 7,655,599 B2 | 2/2010 | Rochling et al. |
| 7,754,655 B2 | 7/2010 | Wolf et al. |
| 7,867,507 B2 | 1/2011 | Birthisel et al. |
| 7,871,645 B2 | 1/2011 | Hall et al. |
| 7,872,077 B2 | 1/2011 | Oetter et al. |

(Continued)

FOREIGN PATENT DOCUMENTS

| | | |
|---|---|---|
| BR | PI 9302980-2 A | 3/1994 |
| BR | 0109913-2 A | 2/2003 |

(Continued)

OTHER PUBLICATIONS

MR Forim, MF das Gracas Fernandez da Silva, JB Fernandes. "Insecticides—Advances in Integrated Pest Management—Chapter 16: Secondary Metabolism as a Measurement of Efficacy of Botanical Extracts: The Use of Azadirachta indica (Neem) as a Model." ISBN: 978-953-307-780-2. pp. 367-390 and additional back page, available online Jan. 5, 2012.*

CH Anjali, Y Sharma, A Mukherjee, N Chandrasekaran. "Neem oil (Azadirachta indica) nanoemulsion—a potent larvicidal agent against Culex quinquefasciatus." Pest Management Science, vol. 68, 2012, pp. 158-163, published May 17, 2011.*

CE Mora-Huertas, H Fessi, A Alaissari. "Polymer-based nanocapsules for drug delivery." International Journal of Pharmaceutics, vol. 385, 2010, pp. 113-142.*

H Fessi, F Puisieux, J Ph Devissaguet, N Ammoury, S Benita. "Nanocapsule Formation by Interfacial Polymer Deposition Following Solvent Displacement." International Journal of Pharmaceutics, vol. 55, 1989, pp. R1-R4.*

ICI Americas. "The HLB System A Time-Saving Guide to Emulsifier Selection." ICI Americas Inc., Revised Mar. 1980, pp. 1-22.*

(Continued)

*Primary Examiner* — Isaac Shomer
(74) *Attorney, Agent, or Firm* — Ladas & Parry LLP

(57) ABSTRACT

A process for obtaining biopolymeric nanoparticles containing *Azadirachta indica* A. Juss (Neem) is described, which comprises, in Phase I, in (10), preparing an aqueous emulsion of Neem oil and extracts, in Phase II, in (20), preparing a biopolymer solution in organic solvent, followed by mixture of both Phases I and II, and, in Phase III, in (30), preparing an aqueous emulsion of a surfactant and adding it to the Phase I and II mixture, affording a nanoparticle suspension which is stabilized. Biopolymeric nanoparticles and powder microparticles obtained are also described.

15 Claims, 8 Drawing Sheets

(56) References Cited

U.S. PATENT DOCUMENTS

Figure 1:
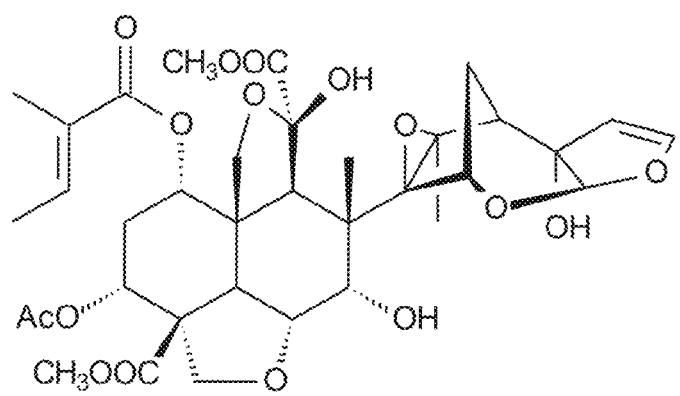

| | | | |
|---|---|---|---|
| 2006/0099233 A1 | 5/2006 | Rao et al. | |
| 2007/0218076 A1* | 9/2007 | Michailovna | C08B 37/00 424/195.17 |
| 2009/0004262 A1* | 1/2009 | Shaw | A61K 9/1623 424/456 |
| 2009/0098200 A1* | 4/2009 | Temtsin Krayz | A61K 9/0095 424/452 |

FOREIGN PATENT DOCUMENTS

| | | |
|---|---|---|
| BR | PI 0508296-0 A | 7/2007 |
| EP | 0 581 467 A1 | 2/1994 |
| WO | 01/76372 A2 | 10/2001 |

OTHER PUBLICATIONS

J Jerobin, RS Sureshkumar, CH Anjali, A Mukherjee, N Chandrasekaran. "Biodegradable polymer based encapsulation of neem oil nanoemulsion for controlled release of Aza-A." Carbohydrate Polymers, vol. 90, 2012, pp. 1750-1756.*

DA Mahmoud, NM Hassanein, KA Youssef, MA Abou Zeid. "Antifungal Activity of Different Neem Leaf Extracts and the Nimonol Against Some Important Human Pathogens." Brazilian Journal of Microbiology, vol. 42, 2011, pp. 1007-1016.*

MY Liauw, FA Natan, P Widiyanti, D Ikasari, N Indraswati, FE Soetaredjo. "Extraction of Neem Oil (Azadirachta indica A. Juss) Using n-hexane and Ethanol: Studies of Oil Quality, Kinetic and Thermodynamic." Asia Research Publishing Network Journal of Engineering and Applied Sciences, vol. 3 No. 3, Jun. 2008, pp. 49-54.*

Irochemical Company. MSDS. http://www.irochemical.com/product/Alginates/Sodium-Alginated.htm accessed Dec. 29, 2016, 3 printed pages.*

Riyajan, As-Ad.; Sakdapipanich, J.T., "Encapsulated neem extract containing Azadiractin-A within hydrolyzed poly(vinyl acetate) for controlling its release and photodegradation stability", Chemical Engineering Journal 152, 591-597, 2009.

Kulkarni, A.R. et al., "Glutaraldehyde crosslinked sodium alginate beads containing liquid pesticide for soil application", J. Control. Release 63, 97-105, 2000.

Shankar, S.S. et al., "Rapid synthesis of Au, Ag, and bimetallic Au core—Ag shell nanoparticles using Neem (Azadirachta indica) leaf broth", J. Colloid Interface Sci. 275, 496-502, 2004.

Tripathy, A. et al., "Process variables in biomimetic synthesis of silver nanoparticles by aqueous extract of Azadirachta indica (Neem) leaves", J. Nanopart. Res. 12, 237-246, 2010.

Prathna, T.C. et al., "Kinetic evolution studies of silver nanoparticles in a bio-based green synthesis process", Colloids Surf. A:Physicochem.Eng.Aspects, 2011, doi:10.1016/j.colsurfa.2010.12.047.

Singh, B. et al., "Controlled release of thiram from neem-alginate-clay based delivery systems to manage environmental and health hazards", Applied Clay Science, 47, 384-391, 2010.

Soppimath, K.S., et al., "Biodegradable polymeric nanoparticles as drug delivery devices", J. Control. Release 70, 1-20, 2001.

Tice, T.R.; Gilley, R.M., "Preparation of injectable controlled-release microcapsules by solvent-evaporation process", J. Control. Release 2, 343-352, 1985.

Ibrahim, H.; et al., "Aqueous nanodispersions prepared by a salting-out process", Int. J. Pharm. 87:239-246, 1992.

Caliceti, P. et al., "Effective protein release from PEG/PLA nanoparticles produced by compressed gas anti-solvent precipitation techniques", J. Control Release 94, 195-205, 2004.

Galindo-Rodriguez, S. et al., "Physicochemical parameters associated with nanoparticle formation in the salting-out, emulsification-diffusion, and nanoprecipitation methods", Pharm Res 21, 1428-1439, 2004.

Tse, G. et al., "Thermodynamic prediction of active ingredient loading in polymeric microparticles", J. Control. Release 60, 77-100, 1999.

Fessi et al., "Nanocasule formation by interfacial polymer deposition following solvent displacement", Int. J. Pharmaceutics 55, R1-R4, 1989.

Liu et al., "Inclusion complexes of azadirachtin with native and methylated cyclodextrins: solubilization and binding ability", Bioorganic & Medicinal Chemistry 13, 4037-4042, 2005.

Goyal, R.N. et al., "Simultaneous determination of adenosine and adenosine-5'-triphosphate at nanogold modified indium tin oxide electrode by osteryoung square-wave voltammetry", Electroanalysis 19, 575-581, 2007.

* cited by examiner

PROCESS FOR OBTAINING BIOPOLYMERIC NANOPARTICLES CONTAINING *AZADIRACHTA INDICA* A. JUSS. (NEEM.) OIL AND EXTRACTS, BIOPOLYMERIC NANOPARTICLES, AND POWDER MICROPARTICLES

RELATED APPLICATION INFORMATION

This application is a 371 of International Application PCT/BR2014/000044 filed 23 Jan. 2014, which claims priority from Brazilian Application No. 102013021210-5 filed on 25 Jan. 2013, the disclosures of which are incorporated in their entirety by reference herein.

FIELD OF THE INVENTION

The present invention belongs in the field of nanoparticle preparation processes for encapsulation of *Azadirachta indica* (Neem) oils and extracts, more specifically, of such a Neem encapsulation process in biopolymer matrices, colloidal suspension, and powder.

BACKGROUND OF THE INVENTION

Products derived from *Azadirachta indica* (A. Juss) (Neem) lead a prominent role in a select group of environmentally correct natural products which are commercially available for controlling insects and pests. Neem is a plant which is tolerant to the most adverse growth conditions, rapidly spreading throughout the globe. Literature reports identify 500 insect species which are sensitive to some kind of Neem extract action.

Currently, biopolymeric nanoparticles make up a more sophisticated agrochemical formulation approach, which renders them suitable for application in the search for novel properties for the correct use of Neem. Among their main advantages in the field, emphasis can be given to their capability of controlling active ingredient rate and release conditions, increasing solubility, reducing contact with active ingredients by farmworkers, and environmental advantages such as reduction of drainage rates.

Such technology allows for managing the external casing properties of a capsule so as to control the moment of release of active substance.

Many papers describe the use of Neem for obtaining metal nanoparticles, and for preparing powder microparticles made with Neem. Studies which use Neem for obtaining metal nanoparticles use only Neem in the process; however, the objective is to provide metal products completely unrelated to the present process.

Agriculture is normally seen as comprising three types of systems: economic, social, and ecologic (or environmental). All the three of them are interconnected, and interactions between agriculture and the environment are complex. Environmental problems such as soil degradation, desertification, destruction of tropical forests, and the resulting decrease in wildlife and pollution of water sources relate to inappropriate agricultural practices or to the intensive use of agricultural inputs.

From Roman times (1$^{st}$ century B.C.) up to the middle of the 20$^{th}$ century, insect control was performed by products derived from plants such as pyrethrin, rotenone, and nicotine (bioinsecticides or natural insecticides). Discovery of DDT (dichlorodiphenyltrichloromethane), initially believed as the solution to insect attacks, was proven a disaster after a long period of use. That gave rise to a search for safe synthetic compounds based on chlorinated hydrocarbons. Such compounds, however, were proven extremely toxic and ecologically disastrous, in addition to rendering insects resistant thereto.

Synthetic pesticides have been used for over 50 years, which makes them the main insecticidal tool. Even though their use has been efficient at controlling some pest species—making it possible to significantly increase food production—, extensive, and sometimes careless, use thereof has triggered many social- and environment-related problems, including contamination of soil, air, water, fish, and man himself; reduction of biodiversity, of the population of natural enemies, of the population and number of bees and other pollinator species, in addition to pest resistance and emergence of secondary pests.

It is estimated that the damage caused by pests in the world production of food, in spite of the efforts made, is still at least one-third of the production.

Another problem to be dealt with is the existent phytosanitary barriers. They are of great importance for the independence of countries regarding crop protection and the population's food safety. Phytosanitary restrictions have imposed food exporting countries the need to master agricultural production technology and to control all steps in the agro-production chain. Brazil, as one of the biggest food producers in the world, has phytosanitary products as one of the essential instruments to the promotion of plant defense.

Nowadays, natural insecticides have become an option and/or a complement to pest control, reducing or eliminating the use of synthetic agrochemicals. Such properties make natural insecticides an important tool for many pest management programs. However, significant production, regulations and application problems must be solved first, in order to enable such products to be reliably purchased in the market.

Among the main limiting problems to the use of natural insecticides, emphasis can be given to the need to identify and study plant species which allow for sustainable exploitation, the influence of seasonal factors and weather conditions, the lack of quality control and reproducibility of the insecticidal action, and the lack of stabilizing mechanisms for the correct use and handling of the active compounds.

Several factors may change the stability of a naturally occurring active product or compound. Each component, either active or inactive, can impact stability depending on the amount.

Other factors, named extrinsic, such as temperature, radiation, light, air (specifically oxygen, carbon dioxide, and water vapors), moisture, harvesting and storage place and time also change stability and content of active compounds.

Furthermore, there are intrinsic factors such as incompatibilities, pH, hydrolysis, racemization e oxidation. For example, rapid degradation of *A. indica* compounds makes them unsuitable for some cultures such as fruit production and gardening (since residual effect normally lasts only from 4 to 8 days). Studies have shown that azadirachtin activity can be reduced to nearly 60% after 4 hours of sunlight exposure, decaying to nearly 50% after 15 hours. Results obtained in the field indicated that *A. indica* extracts applied over the cultures may remain active only for about three days.

In the search for natural insecticides, the Meliaceae family has been identified as one of the most promising groups, once most of its species exhibits multiple actions in pest control. Inside the Meliaceae family, one species in particular is worth mentioning: A. Jussieu's *Azadirachta indica*, popularly known as Nimtree or Neem.

Neem, plant which is original from Myanmar and the arid regions of the Indian subcontinent, present from India to Indonesia, has been introduced throughout the tropical region of the globe. It can currently be found in Asian and African countries, in Australia, tropical North America, Central America, and South America.

Neem is a plant which has been extensively used in several areas, such as medicine, veterinarian medicine, farming, pharmacy, cosmetic and furniture industry, plant reforestation, and the like. It is a tree which is tolerant to the most adverse culture conditions (high temperatures, poor and saline soils, etc.), which is one of the factors that justifies its quick spread all over the world. Among such properties, the greatest current interest involving Neem, mainly in the western world, lies in the insecticidal properties thereof. About 500 insect species have been currently reported as being sensitive to some kind of Neem extract action.

Neem properties are due to a large number of secondary metabolites, mainly triterpenes and limonoids, available in many parts of the plant. Among such compounds, emphasis is given to azadirachtin (FIG. 1), main constituent of the plant and of commercial formulations.

Azadirachtin is a limonoid which is mostly concentrated in the fruits, although it can be found in lesser amounts all over the plant.

Said substance has several biosynthetic oxidations which form many functional groups comprising oxygen, which tends to make this compound more reactive both chemically and biologically.

Previous studies have shown many stability problems and degradation in naturally occurring active compounds. For example, even when stored under optimal conditions, away from humidity, light and temperature, the azadirachtin content in commercial Neem oils decays with time.

Figure 2:
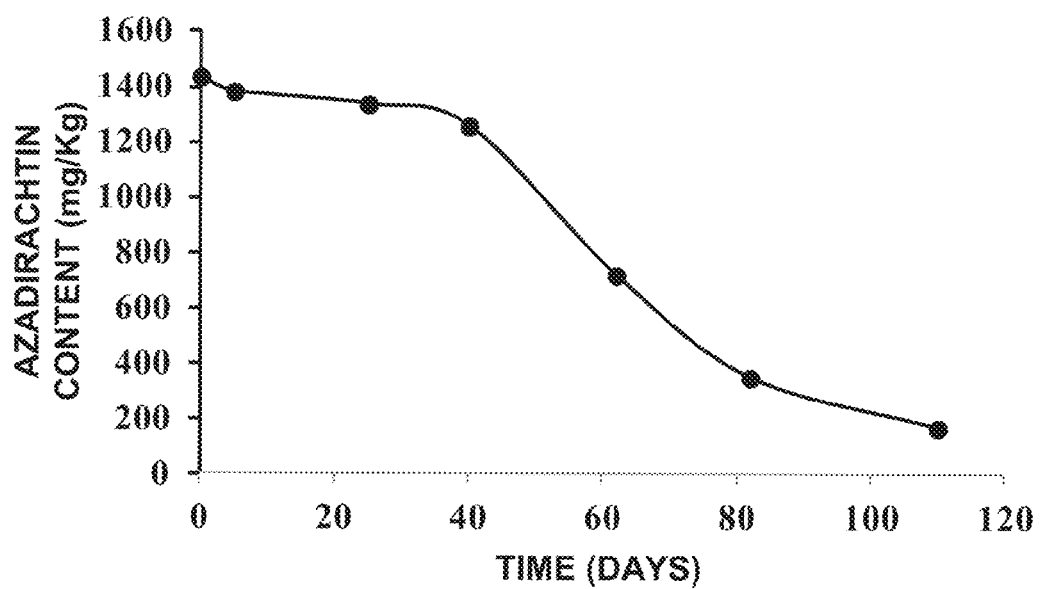

FIG. 2 illustrates the decay curve for azadirachtin.

Neem oil samples subjected to accelerated aging process by UV radiation allow for observing the constant degradation of azadirachtin.

In a closed system, performed under ultraviolet radiation, degradation rate in oil/water samples was approximately 108 times higher than that observed for oil samples without water.

Such results show the degradative action of humidity on the natural product in an ultraviolet radiation catalyzed hydrolysis mechanism. The mechanism is illustrated in the following Equation 1.

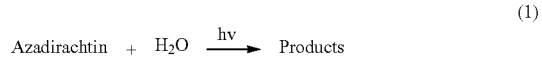

(1)

The presence of functional groups in Neem metabolites such as, for example, epoxide, ether and ester groups, conjugated systems, and the like present in the azadirachtin molecule is liable for its low environmental endurance, the main problem being its sensitivity to photodegradation. Azadirachtin's rapid activity loss limits its use in farming. An insecticide must be persistent enough in order to kill or control insects and pests.

Lack of monitoring methods and quality control has become another limiting aspect to the development and reliable use of natural products. It is impossible to ensure reproducibility of a product's expected action in the absence of production protocols and quality control methods.

Concurrently to the development of (natural or synthetic) biocides, there has been the need for a wide variety of types of formulations, additives and technological processes which enable formulation of active ingredient pesticides with different physical and/or chemical properties.

Formulations aim to promote convenient and safe use of a product which will not deteriorate in a period of time, and which will obtain the maximum activity inherent to an active compound.

More sophisticated formulations based on powerful surfactants and other additives, and better comprehension of the principles of colloid and surface chemistry as to increasing stability and biological activity are in accordance with the operator's needs, environmental safety requirements, and improvement of active compound activity and endurance.

The most common pesticide active ingredient formulations mentioned by GCPF—Global Crop Protection Federation (CropLife International) include granulates (GR), concentrated solutions (SL), emulsible concentrates (EC), wettable powders (WP), concentrated suspensions (SC), oil/water emulsions (EW), microcapsules (CS), etc.

A more sophisticated approach to the formulation of agrochemicals in nanometric scale involves nano- and microencapsulation. Among the main advantages thereof in the field, emphasis can be given to capability to control the conditions in which the active ingredient is released, increased solubility, reduced contact with active ingredients by farmworkers, extended patent validity, and environmental advantages such as drainage rate reduction. Such technology allows for managing the external casing properties of a capsule so as to control the moment of release of active substance.

A large number of different strategies has been proposed in order to modify nano- and microparticle physical-chemical characteristics, and thus their interaction with the biological medium. For example, it is already possible to modify the chemical nature of the particle's polymer matrix by changing some characteristics such as biorecognition, biodistribution, bioadhesion, biocompatibility, mobility, and biodegradation.

Polymeric nanoparticles can be defined as colloidal polymeric particles comprising active compounds. The nanoparticles can be classified in two categories: nanocapsules and nanospheres.

Nanocapsules are carrier compounds formed by an oily core coated by a polymeric wall, the active compound being either in said core or adsorbed in the polymeric wall.

On the other hand, nanospheres consist of a solid polymer matrix which does not have oil in its composition, the compounds being trapped and/or adsorbed.

Both colloids are stabilized by surfactants in the particle/water interface.

Different nano- and microparticle production processes are available and may develop and/or improve physical-chemical characteristics such as size, structure, morphology, surface texture and composition. On that matter, see the publications Soppimath, K. S., et al. Biodegradable polymeric nanoparticles as drug delivery devices. *J. Control. Release* 70, 1-20, 2001; Couvreur, P. et al., Nanocapsule technology. *Crit. Rev. Ther. Drug Carrier Syst.* 19, 99-134, 2002; Tice, T. R.; Gilley, R. M. Preparation of injectable controlled-release microcapsules by solvent-evaporation process. *J. Control. Release* 2, 343-352, 1985; Ibrahim, H.; et al., Aqueous nanodispersions prepared by a salting-out process. *Int. J. Pharm.* 87:239-246, 1992; Caliceti, P. et al., Effective protein release from PEG/PLA nanoparticles produced by compressed gas anti-solvent precipitation techniques. *J. Control Release* 94, 195-205, 2004; Galindo-Rodriguez, S. et al., Physicochemical parameters associated with nanoparticle formation in the salting-out, emulsification-diffusion, and nanoprecipitation methods. *Pharm Res* 21, 1428-1439, 2004.

Colloidal release systems show a great and efficient potential as release systems for one or a mixture of active compounds (plant extracts) at specific action sites (delivery systems), and control over the release rate, thus minimizing undesirable toxic effects and enhancing their physical-chemical stabilities, see Tse, G. et al., Thermodynamic prediction of active ingredient loading in polymeric microparticles. *J. Control. Release* 60, 77-100, 1999.

Biodegradation may occur in a biological system through polymer chain relaxation, break of the monomer unit located at the end of the chain (erosion), or even through random bond breaking at some position along the polymer chain (degradation).

Studies related to nanotechnology described in literature for the species *Azadirachta indica* (A. Juss) (Neem) are as diverse as the nanotechnology theme is vast.

Among the studies which are closest to the research which resulted in the present application is the article by Riyajan, As-Ad.; Sakdapipanich, J. T. Encapsulated neem extract containing Azadiractin-A within hydrolyzed poly(vinyl acetate) for controlling its release and photodegradation stability. *Chemical Engineering Journal* 152, 591-597, 2009. The authors used polyvinyl acetate meshed with 5% (w/v) glutaraldehyde for preparing powder microcapsules containing Neem extracts using the Spray-Drying technique. As a result, powder microparticles were obtained having average diameter greater than 10 µm, about 80% encapsulation efficiency, with enhanced stability (efficiency) against photodegradation.

Another relevant article is the one by Kulkarni, A. R. et al., Glutaraldehyde crosslinked sodium alginate beads containing liquid pesticide for soil application. *J. Control. Release* 63, 97-105, 2000. In this article, the authors describe Neem oil encapsulation in particles formed by sodium alginate polymers meshed with glutaraldehyde. Particle diameter and encapsulation efficiency ranged between 1.01-1.68 and 72-90% respectively.

In the article by Shankar, S. S. et al., Rapid synthesis of Au, Ag, and bimetallic Au core-Ag shell nanoparticles using Neem (*Azadirachta indica*) leaf broth. *J. Colloid Interface Sci.* 275, 496-502, 2004, an environmentally correct extracellular synthesis method is described for the production of metal silver and gold nanoparticles using *Azadirachta indica* leaves.

Tripathy, A. et al., Process variables in biomimetic synthesis of silver nanoparticles by aqueous extract of *Azadirachta indica* (Neem) leaves. *J. Nanopart. Res.* 12, 237-246, 2010 used aqueous *A. indica* leaf extracts for producing silver crystal nanoparticles in biomimetic processes.

Silver nanoparticles have also been produced by Prathna, T. C. et al., Kinetic evolution studies of silver nanoparticles in a bio-based green synthesis process. *Colloids Surf.A: Physicochem.Eng.Aspects*, 2011, doi:10.1016/j.colsurfa.2010.12.047 using Neem leaf extracts applied in kinetic studies.

Electroanalytical measurements of adenosine and adenosine-5'-triphosphate have been determined by Goyal, R. N. et al., Simultaneous Determination of Adenosine and Adenosine-5'-triphosphate at Nanogold Modified Indium Tin Oxide Electrode by Osteryoung Square-Wave Voltammetry. *Electroanalysis* 19, 575-581, 2007 using modified gold nanoparticles in biological systems such as *A. indica* extracts.

Particles containing powder Neem leaves, calcium alginate, kaolin, and bentonite have been prepared in order to control release kinetics, toxicity, and properties of the fungicide Thiram®. In this study, Singh, B. et al., Controlled release of thiram from neem-alginate-clay based delivery systems to manage environmental and health hazards. *Applied Clay Science*, 47, 384-391, 2010 demonstrate an application of Neem in preparing controlled release systems with particles of approximately 1 mm and encapsulation efficiency for Thiram® close to 100%.

There are several studies with patent applications for products and processes involving Neem.

Patent applications in progress at the Instituto Nacional da Propriedade Industrial (INPI)—*National Institute for Industrial Property*—are related to fertilizers, biological activities (germicides, insecticides, bactericides, fungicides, etc.), Neem oil and extract production techniques, granular formulations, repellents, stability studies, deodorization, analytical techniques, etc. However, none of those studies focuses on polymeric nano- and microparticle production techniques applied to increase stability of Neem-derived chemical constituents, or to control the release kinetics thereof in biological medium, which are the objective of the present application.

Patent applications which were filed at INPI involving the species *Azadirachta indica* include the following Published Brazilian Application Nos.: BR0804594-1 A2, BR0804546-1 A2, BR0702226-3 A2, BR0701347-7 A2, BR0502588-5 A2, BR0508296-0 A2, BR0000809-5 A2, BR9307044-6 A2, BR9302976-4 A2, BR9202628-1 A2, BR0502772-1 A2, BR0109913-2 A2, BR0700034-0 A2, BR9305223-5 A2; Utility Model MU8602632-1 U2, and Brazilian Patents BR9302980-2 B1 e BR9302981-0 B1.

Published Brazilian Application No. BR0702226-3 A2 describes the preparation of a Neem emulsible oil using tall oil extracted from Pinnus as emulsifier.

Published Brazilian Application No. BR0508296-0 A2 describes a granular formulation having systemic action when distributed in the rhizosphere. The formulation contains Neem extracts, hydrocarbon wax, clay, and colorant. The azadirachtin content in said study was monitored and controlled according to its concentration in the extracts. Such formulations produced an stabilizing effect in storage and control over field release of azadirachtin.

Brazilian Patent No. BR9302980-2 B1 proposes a method for preparing Neem extracts containing high levels of azadirachtin, which is more stable in said extract.

Among the several diverse extract preparation techniques, Utility Model No. MU8602632-1 U2 introduces an extraction technique which uses ball mills for micronizing Neem seeds in the presence of organic solvents, affording Neem seed microparticles, in fact, ground and micronized seeds.

Published Brazilian Application No. BR0109913-2 A2 describes a completely water soluble organic solvent-free solid form pesticide with Neem extract release system, formulated with saccharides (methylcellulose, sucrose), affording pellets.

International patent libraries also list a great number of Neem-related studies, such as North-American U.S. Pat. Nos. 4,515,785, 4,537,774, 4,556,562, 4,902,713, 4,943,434, 4,946,681, 5,001,146, 5,001,149, 5,047,242, 5,110,591, 5,124,349, 5,229,007, 5,281,618, 5,298,247, 5,298,251, 5,352,672, 5,352,697, 5,356,628, 5,368,856, 5,370,873, 5,371,254, 5,372,817, 5,391,779, 5,395,951, 5,397,571, 5,405,612, 5,409,708, 5,411,736, 5,420,318, 5,472,700, 5,501,855, 5,503,837, 5,602,261, 5,626,848, 5,635,193, 5,663,374, 5,679,662, 5,695,763, 5,698,423, 5,730,986, 5,736,145, 5,756,773, 5,827,521, 5,856,526, 5,900,493, 6,193,974, 6,294,571, 6,312,738, 6,340,484, 6,545,167, 6,602,823, 6,660,291, 6,703,034, 6,703,347, 6,733,802, 6,734,198, 6,746,988, 6,773,727, 6,811,790, 6,824,787, 6,835,719, 6,849,614, 6,855,351, 6,855,351, 6,875,885, 6,930,076, 6,991,818, 7,083,779, 7,112,553, 7,132,455, 7,182,952, 7,186,891, 7,194,964, 7,204,994, 7,250,175, 7,250,396, 7,320,966, 7,345,009, 7,345,080, 7,351,420, 7,361,366, 7,390,480, 7,476,397, 7,514,464, 7,530,196, 7,531,189, 7,534,447, 7,537,777, 7,618,645, 7,622,641, 7,655,597, 7,655,599, 7,674,807, 7,687,533, 7,696,232, 7,722,695, 7,754,655, 7,803,832, 7,803,992, 7,807,679, 7,823,323, 7,867,507, 7,871,645, 7,872,067, 7,887,827 and H1.541.

In general, a lot of those processes relate to extract preparation, azadirachtin extraction, increase in stability, biological activities, fertilizers, formulation, and structural modifications.

Among application results in searches, no technique, process, or formulation component is similar to those described in the methodology which is the object of the present application.

U.S. Pat. No. 6,340,484 describes saccharide pellets saturated with completely water-soluble organic solvent-free Neem extracts, which affords stability and control over the release kinetics.

U.S. Pat. No. 5,856,526 describes the preparation of powder azadirachtin having a purity content close to 90%, and an emulsible concentrate comprising about 30 wt % azadirachtin. According to this patent document, powder azadirachtin was prepared using classic extraction and fractionation phytochemical techniques involving maceration, concentration and chromatographic separation steps, and the emulsible concentrate prepared by dissolving the azadirachtin rich fraction in organic solvents which comprise emulsifiers and sun blocks or not.

Something similar is described in U.S. Pat. No. 5,736,145 for production and purification processes of powder azadirachtin, and for preparation of a stable aqueous composition for storage. For the emulsion formulation, a mixture of alcohol and water, oleic acid, emulsifier, Neem oil and extract, and p-aminobenzoic acid as sun block is used.

U.S. Pat. No. 6,193,974 describes the preparation of microemulsions using non-ionic surfactants for providing the emulsion also comprising p-aminobenzoic acid as sun block. As a result, a stable aqueous composition is obtained, where, depending on the amount of Neem oil and dilutions, different contents of azadirachtin can be found.

Preparation processes for azadirachtin rich extracts and fractions, and stable emulsions for storage are also described in U.S. Pat. Nos. 6,811,790, 5,827,521, 5,695,763, H1541, 5,420,318, 5,411,736, and others.

Despite the great number of published studies describing techniques for producing Neem extracts and fractions and powder azadirachtin, reproducibility of the technique generally depends on seasonal effects, and on the quality of the chosen seed.

There are also several studies which aim at proposing viable compositions for stabilizing formulations made with Neem oil and extracts, and azadirachtin.

Thus, novel alternatives have arisen. U.S. Pat. No. 5,698,423 relates to a procedure for growing plant cells and for producing azadirachtin, and reactors under controllable conditions.

U.S. Pat. No. 6,733,802 describes a formulation for preparing a Neem derived natural insecticide. Said study describes the use of surfactants derived from plants of the *Saponaria, Quillaja, Chlorogalum,* or *Sapindus* genera, and of antioxidants such as vitamin C, tocopherol and other derivatives from the *Zingiber* or *Curcuma* genera.

U.S. Pat. No. 6,703,034 introduces a formulation for preparing microemulsions with Neem oil using non-ionic surfactants such as, for example, alkylphenol etoxylates.

U.S. Pat. No. 6,635,757 introduces powder insecticide formulations comprised by a Neem extract complex comprising azadirachtin with water dispersible cyclodextrines which are dried using a Lyophilizer or Spray-Drying. In said study, several variations in the composition of azadirachtin, solar protection agents (hydroquinone and anacardic acid), and salicylic acid were performed, resulting in formulations which increase the defense mechanism lifetime of such insecticides in crops.

U.S. Pat. No. 6,667,277 describes chemically modified gums which increase biological efficiency for use in several insecticide, herbicide, or fungicide formulations, having several active ingredients, including solid Neem oil, which are dispersed in aqueous medium with rapid release of biological agents.

U.S. Pat. No. 5,643,351 makes use of polymer melts dispersed in water or organic solvents, encapsulating agricultural ingredients with, for example, Neem products in the form of polymeric films. In said patent, polyethylene glycol and styrene oxide and propylene oxide co-polymers, non-ionic surfactants, liquid emulsifiers, dispersion agents, and ultraviolet protectors were used.

U.S. Pat. No. 7,538,079 describes a process for producing, through Spray-Drying, powder capsules formulated with inorganic salts and beneficial agents such as essential oils for perfumes, aromatherapeutic materials, vitamins, insect repellents, etc., possibly having in their composition detergents, polymers, sequestering agents, and diverse oils such as, for example, citronella oil and Neem oil, applied in therapeutic or stimulating processes.

U.S. Pat. No. 5,009,886 introduces a process for producing dentifrice microparticles or microfibers formulated with Neem branch or root extracts.

U.S. Pat. No. 7,872,067 innovates with an amphiphilic polymer composition applied in order to prepare water insoluble compound compositions dispersed in aqueous medium, which are applied in the protection of crops. Azadirachtin is listed among the many insecticides that may be formulated.

U.S. Pat. No. 7,871,645 provides a method and composition with ion exchange resins loaded with one or more active compounds. There are several pesticides and drugs that may be adsorbed in the resins, including azadirachtin.

Carrier particles for several pesticides having diameters between 500 and 3000 micrometers are introduced in U.S. Pat. No. 7,867,507. The process consists of applying a layer of a liquid comprising solvent, specific fixation agent for the groups, bentonite, carbohydrates, proteins, lipids, synthetic groups over powder carbaryl carrier group previously adsorbed with either insecticides, fertilizers, herbicides, or stimulants, comprising adjuvants or not. Azadirachtin lies among the several listed pesticides which are liable to be applied with carrier particles. Among the advantages, the authors give emphasis to environmental impact reduction.

In a similar study, U.S. Pat. No. 7,754,655 describes preparing agrochemical formulations as microcapsules. Microformulation consists of a dispersion particulate phase of polyurea and/or polyurethane microparticles with penetrating agents and, if suitable, additives, said phase being poured onto a suspension of a solid agrochemical active compound, additives (protective colloid and emulsifiers), and water. Azadirachtin is also listed among compounds.

U.S. Pat. No. 7,655,599 and U.S. Pat. No. 7,655,597 describe agrochemical formulations based on emulsifiers and adjuvants, respectively.

U.S. Pat. No. 7,655,599 describes a suitable formulation for several compounds, such as azadirachtin, based on ethylenediamine alkoxylate emulsifier, which acts either as emulsion stabilizer, crystallization inhibitor, or both. If necessary, penetration promoters, emulsifiers, and δ-butyrolactone are added to the formulation.

U.S. Pat. No. 7,655,597 describes a pesticide (insecticide or herbicide) composition which is formulated with adjuvant or additive co-polymers, where the co-polymer consists of individual proportions of maleic or itaconic groups. Such formulation promotes efficiency gain when compared to the non-formulated active compound, which allows it to be applied for azadirachtin.

Excellent stability for water dispersed granulated solid formulation was achieved according to U.S. Pat. No. 6,596, 292. The formulation comprises active compound, including azadirachtin, dispersant, wetting agent, boron, water-soluble carrier, and smectite.

SUMMARY OF THE INVENTION

Figure 10:
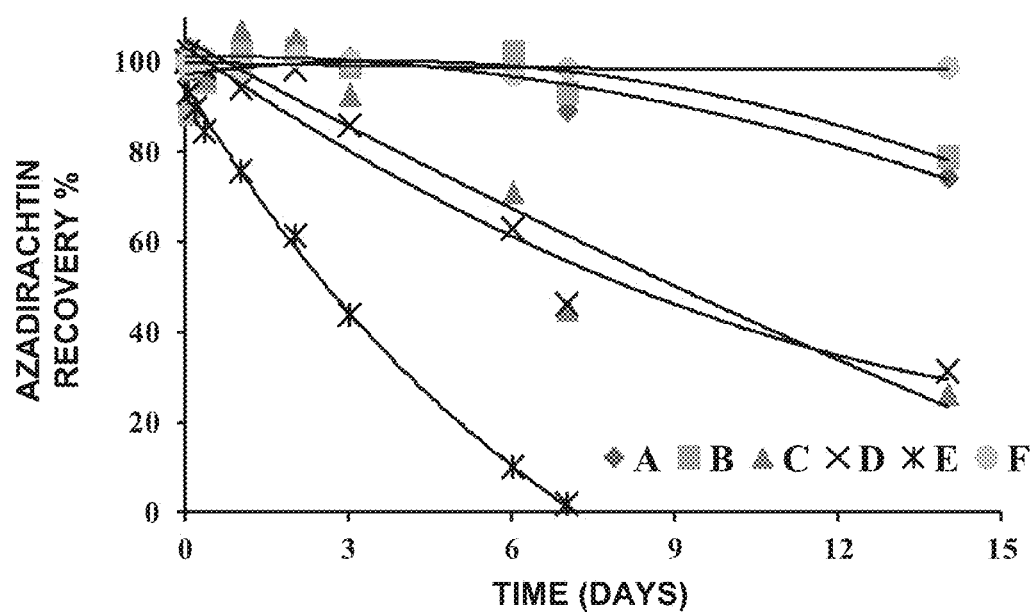

In a broad aspect, the present process for obtaining biopolymeric nanoparticles comprising oil enriched with *Azadiractha indica* (A. Juss.) (Neem) extracts comprises the steps of:

a) Providing Neem oil, from ground Neem almonds, enriched with Neem extracts;

b) Phase I: forming an oil/water nanoemulsion obtained by vigorously stirring, in the aqueous dispersion medium, Neem extracts, internal constituents containing a non-ionic surfactant or not;

c) Phase II: wherein an acetone or acetone/ethanol solution comprising a previously dissolved biopolymer is slowly poured, aided by a peristaltic pump, onto the nanoemulsion from step a) under stirring, affording a combination (Phase I+Phase II);

d) Phase III, wherein, following a stabilization period of 10 minutes, a third aqueous phase comprising a high hydrophilic-lipophilic balance surfactant is added onto the combination (Phase I+Phase II) under stirring so as to ensure stability of the afforded colloidal dispersion;

e) Moderately stirring for 10 minutes, and more 30 minutes of setting;

f) Adjusting the colloidal dispersion final volume by removing the organic solvent and part of the water in vacuum; and g) Recovering the biopolymeric nanoparticles comprising *Azadiractha indica* (A. Juss.) oil extracts in colloidal dispersion.

Thus, the present application provides a process for obtaining biopolymeric nanoparticles containing oil, alternatively oil enriched with *Azadirachta indica* A. Juss. (Neem.) extracts from Neem extract, and for preparing an oil enriched in azadirachtin content, azadirachtin quality control in raw materials and in formulated products, and for formulating biopolymeric nanoparticles with Neem extracts and oil in colloidal suspension.

The invention also provides a process for providing biopolymeric nanoparticles with Neem oil and extracts which successfully recovers azadirachtin without degradation steps while exhibiting high encapsulation efficiency, which is necessary in order to increase ultraviolet stability and dispersion capability in aqueous medium.

The invention also provides a process for providing biopolymeric nanoparticles with Neem oil and extracts which is easy to implement and is cost-efficient.

The invention also provides a process for providing polymeric nanoparticles with Neem oil and extracts which allows for forming biopolymeric nanocapsules, i.e., capsules in nanometric scale.

The invention also provides a process for providing polymeric nanoparticles with Neem oil and extracts which uses reduced surfactant amounts.

The invention also provides a process for providing polymeric nanoparticles with Neem oil and extracts which eliminates the use of synthetic sun blocks.

The invention also provides a process for providing polymeric nanoparticles with Neem oil and extracts which allows for analytical control over the active compound content.

The invention also provides a process for providing polymeric nanoparticles with Neem oil and extracts based on low-cost commercial biodegradable polymers which eliminate the need of derivatization steps, having commercial and environmental impacts.

The invention also provides a process for providing polymeric nanoparticles with Neem oil and extracts wherein the small diameter of the resulting nanoparticles allows for greater cell penetrability, ingestion by insects, plant systemic action, and the like, having a positive impact over biological efficiency.

The invention also provides colloidal suspensions of Neem oil and extracts with biopolymers, and optionally surfactants.

The invention also provides the biopolymeric nanoparticles comprising Neem oil and extracts for agricultural use.

The invention further provides powder microparticles.

BRIEF DESCRIPTION OF THE DRAWINGS

Appended FIG. 1 shows the chemical structure of the limonoid azadirachtin.

Appended FIG. 2 is a graphic showing the azadirachtin degradation curve in *A. indica* oils.

Appended FIG. 3 shows Chromatograms of nanoparticles in colloidal suspension: without (FIG. 3A) and with Neem extracts (FIG. 3B).

Appended FIG. 4 shows a simplified flow chart of the inventive process.

Appended FIG. 5 is a graphic which shows pH variation of the Neem nanocapsule formulation in a storage period of 0 to 90 days at room temperature.

Appended FIG. 6 is a bar chart showing the particle diameter investigation in formulations containing different amounts and types of polymers.

Appended FIG. 7 shows photomicroscopies of PCL nanoparticles loaded with 2% (m/v) Neem oil. Magnifications: a) 10.000×; b) 25.000× and c) 50.000×.

Appended FIG. 8 shows photomicroscopies of Neem nanocapsule powder microparticles. Magnifications: a) 1.000×; b) 10.000× and c) 50.000×.

Appended FIG. 9 shows TG (FIG. 9A) and DTG (FIG. 9B) curves obtained for different Neem nanoparticle formulations, wherein: A) NC-30 (PCL, isodecyl oleate); B) NC-32 (PCL, Neem oil); C) NC-34 (PCL, Neem oil and extract); D) NC-36 (Neem oil and extract) e E) NC-37 (Neem extract, isodecyl oleate).

Appended FIG. 10 shows azadirachtin recovery curves after ultraviolet radiation of: A) Powder nanocapsules without Span®60; B) Powder nanocapsules with Span®60; C) Nanoparticles in colloidal suspension without Span®60; D) Nanoparticles in colloidal suspension with Span®60; E) Neem oil and F) Neem oil protected from UV radiation for an initial azadirachtin content of 2.800,0 mg $Kg^{-1}$.

Figure 11:
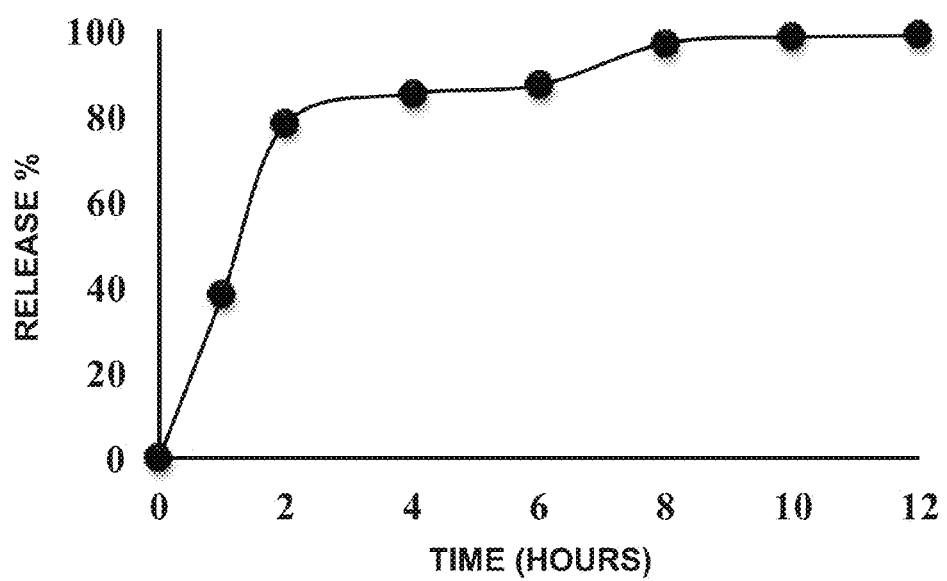

Appended FIG. 11 is a plot of the profile of PCL nanoparticle azadirachtin bulk release in colloidal suspension (n=3).

DETAILED DESCRIPTION OF THE INVENTION

The inventive process for providing biopolymeric nanoparticles comprising *Azadiractha indica* (A. Juss) (Neem) oil and extracts involves preparation of said oils and extracts, biopolymers for encapsulating said oils and extracts, and optionally surfactants for preparing an oil emulsion.

Therefore, a first object of the invention is a process for providing biopolymeric nanoparticles comprising *Azadiractha indica* (A. Juss) (Neem) oil and extracts.

A second object of the invention is colloidal suspensions which result from the present process.

A third object of the invention is nanoparticles comprising *Azadiractha indica* (A. Juss) (Neem) oil and extracts obtained by evaporation of solvent and part of the water in said colloidal suspension.

A fourth object of the invention is powder microparticles resulting from Spray-dryer evaporation of the nanoparticles in colloidal suspension combined with a drying excipient proportion, including but not limited to colloidal silica.

Useful for the implementation of the present invention are non-polluting and non-toxic polymers when forming colloidal suspensions, such as biodegradable and biocompatible polymers (biopolymers) selected from: gelatin, chitosan, sodium alginate, cyclodextrines, and aliphatic polyesters. Among such compounds are: lactate and glycolate homo- and co-polymers (PLA, PGA, PLGA), poly-ϵ-caprolactone (PCL) and polyhydroxyalkanoates, known as PHA, cellulose, cassava starch, and the like.

Such polymers can be degraded by enzymatic action or hydrolysed, showing agricultural and pharmaceutical applications. Biodegradable polymers cooperate with environmental actions once they are decomposed in field without leaving residues.

Furthermore, poly-methyl methacrylate (PMMA), used in the pharmaceutical industry for its biocompatibility properties, can be applied to living beings, even though it is not biodegradable, and, therefore, it is a useful polymer for the purposes of the invention.

Useful surfactants for the implementation of the invention include surfactants which promote quick hydrophilic-lipophilic balance such as sorbitan monostearate (Span® 60) and polysorbate (Tween™ 80).

Biological activity directly depends on qualitative and quantitative characteristics of the plant extracts, which can in turn be controlled by means of techniques such as, for example, extract enrichment.

In this case, the initial task is to ensure the formulation's reproducibility.

Therefore, the first step for preparing the nanoparticles comprises preparing and analyzing Neem oils and extracts used in the process, the main parameter to be considered being the final azadirachtin content.

The raw material used for producing the biopolymeric nanoparticles mainly comprises Neem almonds, although other parts of the plant are equally useful.

The extraction procedure used in the present application involves maceration of Neem almonds with n-hexane followed by extraction with ethanol.

According to this technique, the oil is initially removed from the almonds by diffusing solvent (n-hexane) through cell walls, which is immediately dissolved following contact.

Diffusion rate is directly proportional to an exponent of the diameter of the particles under maceration with free solvent flow; that is why it is important to grind the almonds. Average particle diameter of the almonds subject to extraction is in the range of 10 to 30 μm. Use of a shaft mechanical stirrer in the percolation process helps micronizing the almonds in even smaller sizes than those obtained through mill grinding, which facilitates the diffusion process.

The extraction process with n-hexane gives Neem oil and a solid cake as byproduct.

Once all the oil has been removed, a second extraction step with ethanol begins.

Exhaustive azadirachtin extraction is conducted by macerating, in ethanol, the solid product (cake) obtained after percolation with n-hexane. Ethanol easily diffuses between cell walls, shows great affinity for limonoids, is low-cost and easy to convert in industrial level. Furthermore it is considered a modern mixture solvent, volatile in nature, fairly inert to solutes, and does not irritate human skin.

Initial removal of non-polar compounds with n-hexane aids solute/solvent (azadirachtin/ethanol) interaction in the cake extraction step with ethanol. Furthermore it enables obtaining solid extracts, easily handled and with greater contents in the active principle content/extract amount ratio. Such characteristics are important for steps of formulation of enriched oils and nanoparticles.

Process yield (% m/m), extraction efficiency (%) and total amount of afforded extract (g) for the prepared extracts are detailed in the following Table 1.

Azadirachtin content in Neem extracts and oil is quantified by CLAE (HPLC—High Performance Liquid Chromatography) after analytical validation, samples being prepared according to Published Brazilian Application No. BR0700034-0A, by the same author of the present application.

Initial analysis of Neem almond quantified azadirachtin content as 2,912.2 mg per almond Kg, making it possible to calculate the process yield.

TABLE 1

| Amount of Almonds | Amount of oil % (m/m) | Amount of extract (% m/m) | Azad. Content (mg · $Kg^{-1}$ ext.) | Extract Efficiency (%) | Azad. Content (mg · $Kg^{-1}$ oil) | Oil Efficiency (%) |
|---|---|---|---|---|---|---|
| 1,040 g | 505.6 g 48.6 | 21.4 g 2.06 | 56,471.0 | 39.9 | 419.1 | 7.0 |
| 1,119 g | 495.0 g 44.2 | 19.1 g 1.71 | 61,698.6 | 36.2 | 322.5 | 4.9 |
| 1,105 g | 519.3 g 47.0 | 19.8 g 1.79 | 58,100.0 | 35.8 | 344.9 | 5.6 |

Coefficient of variation between chromatographic analyses (triplicates) was lower than 6%; Azadirachtin content in almonds was 2,912.2 mg $Kg^{-1}$.
Azadirachtin content obtained through the extraction method considered standard.

Validation of the analytical method was performed following criteria proposed by ICH (International Conference on Harmonization). Figures of merit investigated in the validation of the method were linearity, selectivity, accuracy, precision, resistance, recovery, quantification and detection limits, and reproducibility.

Figure 3A:
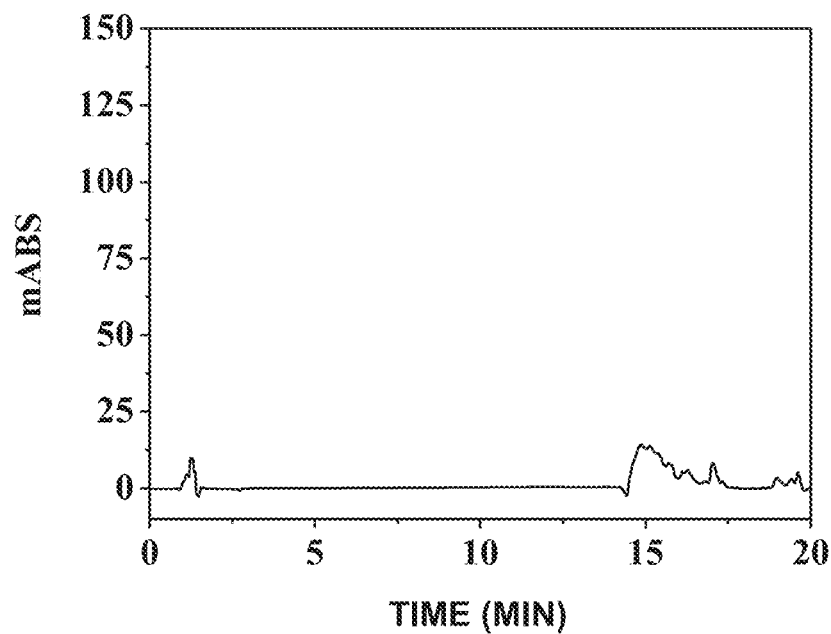
Figure 3B:
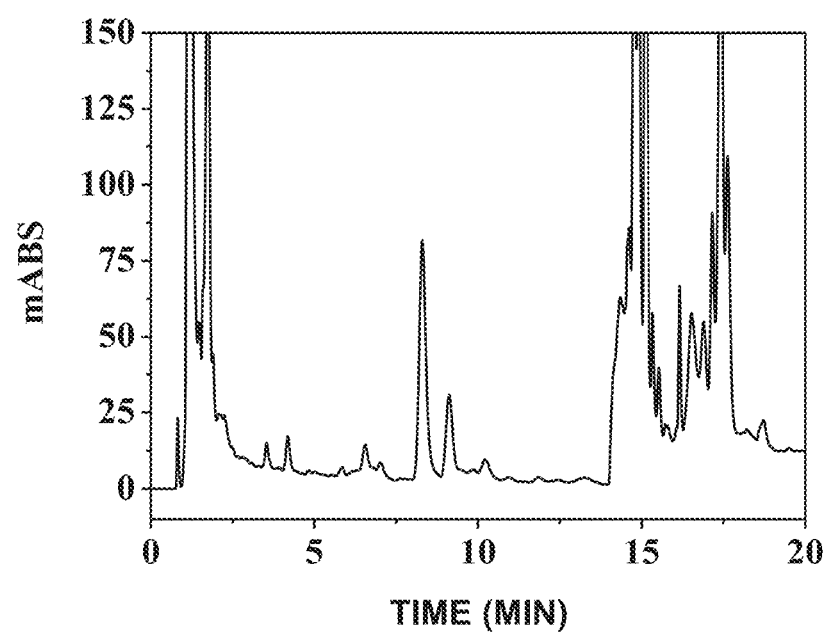

Selectivity of the analytical method was evaluated by comparing analysis chromatograms of nanoparticles prepared with Neem extracts and oils as in FIG. 3B, and nanoparticles without such oils and extracts, FIG. 3A. No interfering peak was observed in 8.68 min for the blank chromatogram (retention time for azadirachtin) in the work wavelength of 217 nm.

Thus, the present analytical method can be considered selective, allowing it to distinguish between the analyte of interest outcome and the other mixture components.

Linearity of the analytical method proposed to quantify azadirachtin through CLAE is confirmed by a calibration curve made with standard azadirachtin solutions (n=7), affording the correlation coefficient ($r^2$) through the method of least squares $r^2$=0.9999.

In addition, the response factor versus the azadirachtin concentration in standard samples (n=7) reveals a (0.045) slope close to zero and a Relative Standard Deviation of 2.98%, showing the linearity of the work range.

Accuracy [Accuracy=(concentration measurement/nominal concentration)×100, n=15] can be evaluated by calculating the recovery percentage of azadirachtin. Great harmony was found between experimental data and theoretical nominal values.

Precision analysis [Accuracy=(concentration measurement/nominal concentration)×100, n=15] made it possible to identify the extension of random errors during sample preparation and method validation. Obtained results show good precision for the analytical method. The Quantification Limit for the method was set at 1.0 $\mu g\ mL^{-1}$, whereas the Detection Limit was 0.3 $\mu g\ mL^{-1}$.

The same azadirachtin validation procedures were carried out for 3-tigloylazadirachtol. Validation results for 3-tigloylazadirachtol were similar to those described for azadirachtin.

Reproducibility, Resistance, Recovery, and Storage Stability

Reproducibility was investigated by analyzing a same nanoencapsulated azadirachtin sample ten times. This result showed correlation between subsequent analyses over the same chromatographic parameters and equipment. Calculated DPR % (Relative Standard Deviation) was 0.71% (n=10).

Resistance of the analytical method was determined by analyzing the same azadirachtin sample (95.0 $\mu g\ mL^{-1}$) in PCL polymeric nanoparticle colloidal suspension under small modifications in chromatographic conditions. Such evaluation aimed at proving that small variations in the method due to deliberate changes in critical parameters are insignificant in the evaluation processes in study, by monitoring possible changes.

Results indicate that there has not been loss in selectivity in chromatographic separation and quantitative information. The small variation in retention time can be justified by changes in solute/solvent/adsorbent interaction. No other variation has been observed, showing that the method is resistant to small variations in chromatographic parameters.

Method recovery has been determined by comparing the results of the total azadirachtin content added and quantified in colloidal suspensions prepared with different biopolymers (PCL, PHB, PMMA).

Recovery results were obtained through the ratio between the quantified azadirachtin content and its nominal concentration expressed in percentage. The average calculated value of the three different formulations (95.0 $\mu g\ mL^{-1}$) was 99.5±7.1% (n=9), showing that there was no analyte loss during the steps of nanoparticle preparation, pre-treatment, or chromatographic analyses.

Azadirachtin solutions stores at 4° C. were considered stable.

Sample Preparation

Pre-treatment is possibly the most important step in quantitative analyses. This is the critical step in chromatographic analyses, usually being the slow step and with greater possibilities of analytical loss in the process. This step involves extraction of active compounds and removal of interferent.

Hence, it was necessary to develop sample opening and pre-treatment methods without compromising recovery. Thus, for analysis of total azadirachtin amount in biopolymeric nanoparticles in colloidal suspension, a technique for polymer dissolution in acetone with subsequent separation of polymer and supernatant was devised.

The ideal solvent must, at the same time, dissolve the polymer and solubilize azadirachtin without equilibrium. After solubilization, the polymer is separated from the supernatant by centrifugation.

The process of drying the samples and solubilizing in methanol before they are analyzed through CLAE avoids impairment of the separation efficiency by polymer residues, and premature loss of the analytical column, once those residues are not soluble in methanol.

Sample preparation for encapsulation efficiency analysis is simpler, once there is no need to remove polymer or open the sample.

However, it was necessary to develop a protocol for nanoparticle separation from the dispersion medium. Once the medium and nanoparticles are separated, it is possible to quantify all of the azadirachtin dissolved in such medium.

Samples in aqueous medium were dried and re-suspended in methanol in order to keep the molar absorption coefficient of azadirachtin constant compared to standard solutions used in making the calibration curve.

Finally, it was also necessary to develop a method to analyze azadirachtin content in powder microparticles.

Similarly to recovery, it was necessary to dissolve the polymer in a suitable solvent (acetone) by dispersing the previously encapsulated azadirachtin. Once dissolved, the polymer and drying excipient were separated from the supernatant by centrifugation. Part of the supernatant was dried out and re-suspended in methanol for chromatographic analyses.

Extraction and pre-treatment of Neem seed and oil samples were carried out according to the method proposed by Forim, M. R.; et al. Simultaneous quantification of azadirachtin and 3-tigloylazadirachtol in Brazilian seeds and oil of *Azadirachta indica*: application to quality control and marketing. *Anal. Methods* 2, 860-869, 2010. Those methods are described in detail hereinafter in the present specification.

Polymeric Nanoparticle Preparation

Neem nanoparticles in the form of powder and colloidal suspension were successfully produced.

Agrochemical products are conventionally applied on field by spraying, water being used as vehicle. However, only a small portion of the agrochemical products really reaches the expected target, not rare in a concentration which is lower than the minimum effective concentration required due to problems such as leaching, photodegradation, hydrolysis, and microbial degradation. Accordingly, repeated applications are necessary, causing direct environmental impacts over the soil and water.

Nanoparticles for agricultural use must be designed so as to satisfy physical and chemical properties which result in improved agricultural pest control and decrease in environmental risks. Among the benefits, emphasis is given to adjusting aqueous dispersion capability of organic compounds with decrease in surfactant use, increase in stability against photolysis-, thermolysis and hydrolysis-induced degradation, and active compound release control, improving the desired biological activity. Accordingly, with the increase in stability and adjustment of biological activity, there is a reduction in dosage and in the need of re-application, which causes direct positive impact on the environment.

Moinard-Chécot, D.; et al. Mechanism of nanocapsules formation by emulsion-diffusion process. Journal of Colloid and Interface Science 317, 458-468, 2008 describe a nano-encapsulation mechanism through a process called emulsion-diffusion, which was used as reference. According to such process, an oil, polymer, and ethyl acetate emulsion is initially prepared. Dilution with pure water allows the ethyl acetate to be diffused out of the droplets, leaving a nanocapsule suspension at the end. It has been demonstrated that the nanocapsule size is related to the organic phase chemical composition and the primary emulsion size by means of a simple geometric relationship. As a result, the majority of the nanocapsule properties is determined in the emulsification step. Organic solvent stepped diffusion takes place by subsequent partition equilibria of ethyl acetate between the droplets and the aqueous phase.

The present process for providing Neem capsules, in its turn, comprises preparing three different phases: a) emulsion in aqueous phase, b) organic phase with an encapsulation polymer, and c) aqueous phase with a surfactant.

As a result, initially there is the incorporation of the molecules which are intended to be encapsulated in a nanoemulsion, followed by polymer coating forming nanoparticles, and, at last, stabilization of the colloidal suspension with a surfactant.

In previously described methods, formation and vesicle incorporation of the molecules which are intended to be nanoencapsulated, polymer coating, and stabilization processes occur in only one step.

Initially, Neem extracts are using for enriching the oil by controlling the azadirachtin content present in the formulation and final product.

Even though the preferred aspect of the invention comprises use of oil combined with Neem extracts, the inventive concept alternatively predicts a formulation comprising only azadirachtin oil, without the addition of extracts for enrichment thereof.

In the case of using the extract for enriching the oil, the necessary amount is determined following chromatographic analyses of the azadirachtin content. For example, an oil with azadirachtin content of 419.1 mg $Kg^{-1}$ can be enriched with 28.0 g of a 56,471.0 mg $Kg^{-1}$ extract at a final content of 2,000 mg $Kg^{-1}$. (Necessary amount of azadirachtin for 2,000 mg in 1 Kg of oil=2,000-419.1=1,581 mg; extract g=1,581×1,000 g/56,471 mg=28.0 g to be incorporated in 1 Kg of oil).

Thus, use of different amounts of extracts with different azadirachtin oil content enables obtaining colloidal suspensions and powder products with different azadirachtin contents, i.e., products with 1,000, 2,000, 10,000 mg $Kg^{-1}$ azadirachtin.

Figure 4:
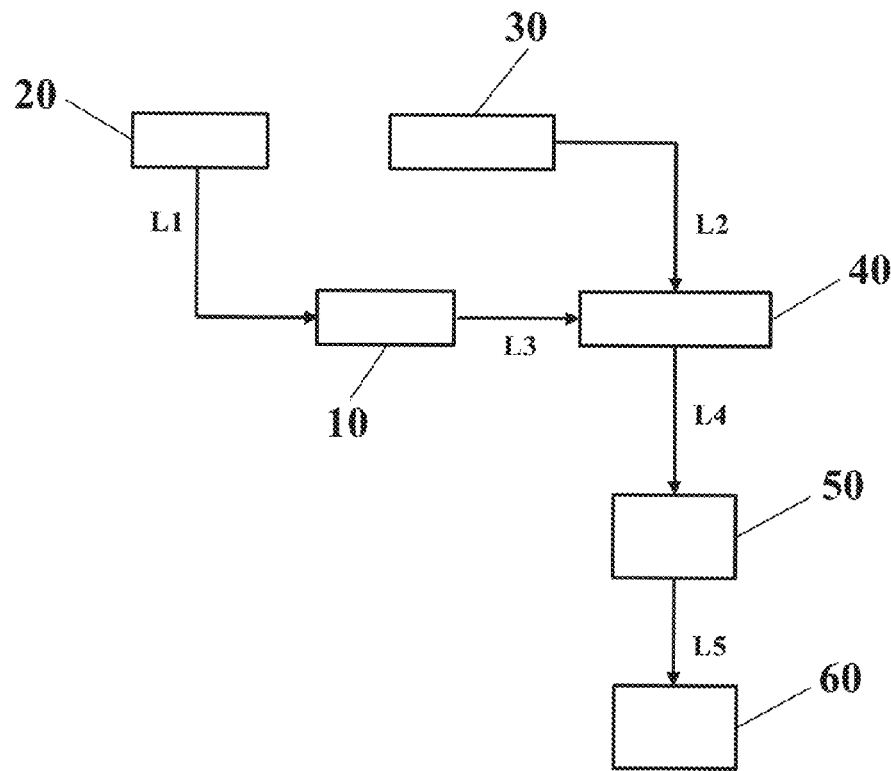

According to the scheme in FIG. 4, oil enriched with Neem extracts is subsequently dispersed in (10) under vigorous stirring in aqueous phase (Phase I) for two to seven minutes, typically five minutes. This system enables the formation of micelles with Neem oil, which creates an emulsion. Due to the solubility difference between the aqueous phase and the micelles, Neem extract constituents remain in micellar phase, not being dispersed into the aqueous phase.

In Phase I, use of surfactants such as non-ionic surfactant sorbitan monostearate Span®60 is optional, which enhances the environmental characteristics of the formulation. The possible elimination of such surfactant already poses improvement over the nanoprecipitation method. Not using the surfactant reduces production cost and possible environmental impacts.

In Phase I the oil content ranges from 0.5 to 10% (m/v), the extract content from 0.1 to 5% (m/v), and the surfactant content from 0.1 to 2% (m/v).

A typical formulation is as follows:

Phase I: [Oil]=2% (m/v), [extract]=0.5% (m/v) and [Span®60] 0.5% (m/v) in aqueous medium (200 mL).

A second phase (Phase II) is prepared in (20) by dissolving a biopolymer in water miscible organic solvent selected from acetone or a mixture of acetone and ethanol in any proportion.

Biopolymer dissolution occurs under heating of 40-50° C., typically 45° C. and stirring.

A typical formulation for Phase II is as follows: dissolving from 0.1 to 2 g of polymer, typically 1.0 g of polymer, for example, PCL, in 200 mL of organic solvent comprised by the mixture of acetone and ethanol in acetone proportions ranging from 100% (0% ethanol) to 30% (70% ethanol).

Once the polymer is dispersed in the organic phase, this phase is slowly poured onto the Phase I emulsion via L1. With diffusion of the organic solvent into the aqueous phase via L3, deposition of the polymer in the oil-water interface takes place, resulting in (40) upon mixture of Phase I+Phase II, yielding the nanoparticles in the form of nanocapsules.

Finally, a third phase (Phase III) in (30) comprised by water and a non-ionic surfactant is prepared and poured, via L2, onto the pre-formed nanocapsules in (40), enabling the surfactant to adsorb onto the nanoparticles, acting as dispersant.

Phase III surfactant is a non-ionic emulsifier surfactant, for example, polysorbate 80, known as Tween®80, derived from sorbitan polyethoxylate and oleic acid. Polysorbate 80 is viscous and soluble in liquid medium.

A typical formulation for Phase III is as follows: dispersing from 0.1 to 2 g of surfactant, typically 1.0 g of surfactant, in 100 mL of distilled water.

Finally, the solvent and part of the water are removed by evaporation under reduced pressure via L4, adjusting the final volume and the azadirachtin content in the dispersion medium, affording the desired product in (50): a nanoparticle comprising Neem oil and extracts in colloidal suspension.

The nanoparticle (50), when subject to drying processes with the aid of an excipient selected from colloidal silica and similar excipients via L5, allows for obtaining a powder microparticle (60).

The nanoparticle (50) to excipient ratio is between 1:0.2 to 1:2 m/m nanoparticles to silica. Formulation component type and content were varied throughout the Applicant's experiments which led to the present application.

The present process still comprises an embodiment in which powder microparticles are directly produced, in which case Phase III of preparation of the emulsifier aqueous solution, and addition thereof via L2 to the mixture of Phase I and II are dispensable. The colloidal suspension obtained by mixing Phase I and Phase II is directly transformed, in this embodiment, into nanoparticles in (40), has its volume reduced for obtaining nanoparticles (50), and is transformed in powder nanoparticles (60) by Spray-Drying.

The extracts can be used for further enriching the azadirachtin content in colloidal suspensions.

Use of Span®60 or another surfactant is optional.

Phase II: [Polymer]=0.5% (m/v) in organic phase (200 mL).

Phase III: [Tween®80]=1.0% (m/v) in aqueous medium (100 mL).

After preparing the nanocapsules and adjusting the final volume of the dispersion aqueous medium (200 mL), the typical final formulation is as follows:

Dispersion medium: [Oil]=2% (m/v), [extract]=0.5% (m/v), [Span®60] 0.5% (m/v), [Polymer]=0.5% (m/v) and [Tween®80]=0.5% (m/v).

The invention will be hereinafter described in reference to specific Examples, but which should not be considered as limiting of the invention.

Biopolymeric nanoparticles have been synthesized in an efficient and reproducible way by using the inventive process.

Illustrative examples are listed below in Table 2.

EXAMPLES

TABLE 2

| | Phase I | | | | Phase II | | Phase III | | |
|---|---|---|---|---|---|---|---|---|---|
| EX. | Neem Oil (g) | Neem Extract (g) | Span ®60 (g) | Water (mL) | Solvent (mL) | PCL (g) | Tween ®80 (g) | Water (mL) | Final Vol. (mL) |
| 1 | 4.0 | 1.0 | -o- | 200.0 | 200.0 | 1.0 | 1.0 | 100.0 | 200.0 |
| 2 | 4.0 | 1.0 | 1.0 | 200.0 | 200.0 | 1.0 | 1.0 | 100.0 | 200.0 |
| 3 | 2.0 | 1.0 | -o- | 200.0 | 200.0 | 1.0 | 1.0 | 100.0 | 200.0 |
| 4 | 2.0 | 1.0 | 1.0 | 200.0 | 200.0 | 1.0 | 1.0 | 100.0 | 200.0 |
| 5 | -o- | -o- | -o- | 200.0 | 200.0 | 1.0 | 1.0 | 100.0 | 200.0 |
| 6 | -o- | -o- | 1.0 | 200.0 | 200.0 | 1.0 | 1.0 | 100.0 | 200.0 |

Measurements of pH, particle diameter (hydrodynamic diameter), polydispersion and zeta potential are parameters which indicate stability of the colloidal suspension.

The pH value of the colloidal systems may affect stability thereof, since changes in this parameter may be related to polymer degradation, degradation of some other formulation component, or even to active substance diffusion into the medium. Changes in pH may also affect the release rate of the active compound or catalyze degradation reactions.

Particle diameter and its distribution size may affect the system's colloidal stability, release kinetics, loading capability, in vivo distribution (systemic action), and toxicity.

Polydispersion, or polydispersity index—IP, indicates nanoparticle average size distribution, and, normally, values lower than 0.2 for the colloidal suspension are considered good stability indicators.

In its turn, zeta potential reflects the surface charge of the nanoparticles, this being the parameter which is influenced by particle composition, dispersing medium, pH, and ionic strength of the colloidal suspension. Normally, nanoparticles with zeta potential values ≥30 mV in module show good colloidal stability in suspension.

The increase in amount of oil leads to the formation of nanocapsules with slightly greater particle diameter. In this pattern, presence and quantity of surfactants were observed to not affect particle diameter.

Zeta potential showed that all formulations exhibit negative charges with values that range from −25.22 and −36.80 mV, typically observed in systems comprising oils with free acid groups. Those zeta potential values combined to low polydispersity indices lead to a stable colloidal dispersion due to repulsion between particles, which inhibits clustering thereof.

The main formulation component, Neem oil, may comprise negatively charged free acids or phospholipids, which grants negative charges to the nanoparticles.

Nanoparticles typically have particle diameter between 30 and 500 nm, pH between 4.0 and 7.0, polydispersity between 0.03 and 0.600, and zeta potential between −10 and −50.0.

Particle diameter, pH, polydispersion and zeta potential values for a series of Examples of Neem nanocapsules prepared through the method described can be observed in Table 3.

TABLE 3

| Example* | pH | Particle Diameter (nm) | Polydispersity | Zeta Potential (mV) |
|---|---|---|---|---|
| 1 | 4.87 ± 0.19 | 231.3 ± 18.89 | 0.490 ± 0.180 | −36.80 ± 0.167 |
| 2 | 4.84 ± 0.11 | 243.0 ± 19.03 | 0.029 ± 0.007 | −29.94 ± 4.439 |

TABLE 3-continued

| Example* | pH | Particle Diameter (nm) | Polydispersity | Zeta Potential (mV) |
|---|---|---|---|---|
| 3 | 4.77 ± 0.17 | 213.3 ± 11.51 | 0.321 ± 0.082 | −25.22 ± 2.104 |
| 4 | 4.95 ± 0.12 | 212.5 ± 10.37 | 0.005 ± 0.002 | −28.54 ± 2.961 |
| 5 | 6.53 ± 0.11 | 177.4 ± 12.38 | 0.227 ± 0.079 | −33.47 ± 2.077 |
| 6 | 6.69 ± 0.13 | 244.9 ± 15.87 | 0.119 ± 0.024 | −32.84 ± 2.736 |

*Values express average result ± standard deviation (n = 3).

Neem oil reduces the dispersion medium pH. However, little did the variation in the amount of oil in the formulations affect the pH value.

Also, little do surfactants affect the pH of colloidal suspensions.

Figure 5:
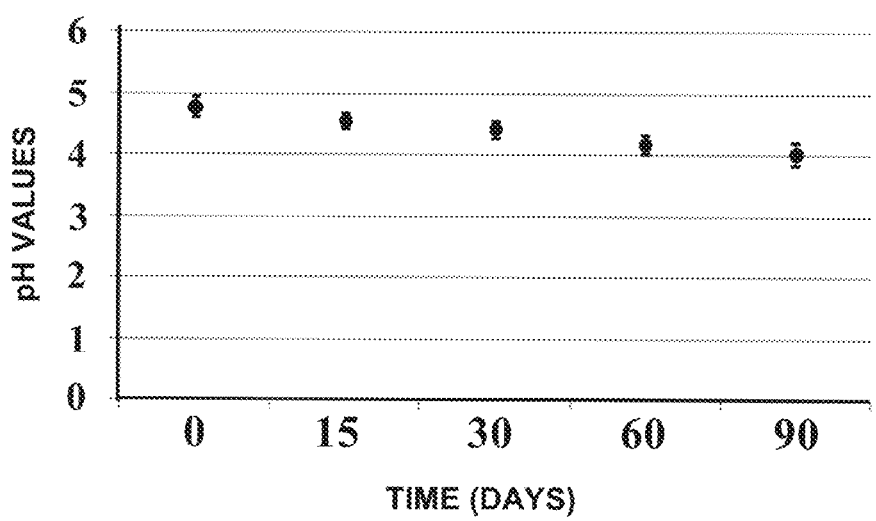

From FIG. 5, it can be observed that pH is reduced with time. pH reduction due to storage at room temperature can be explained by polymer degradation.

It was observed that the particle diameter is more dependent on the amount of oil and extract than on the amount or type of polymer used for encapsulation.

Figure 6:
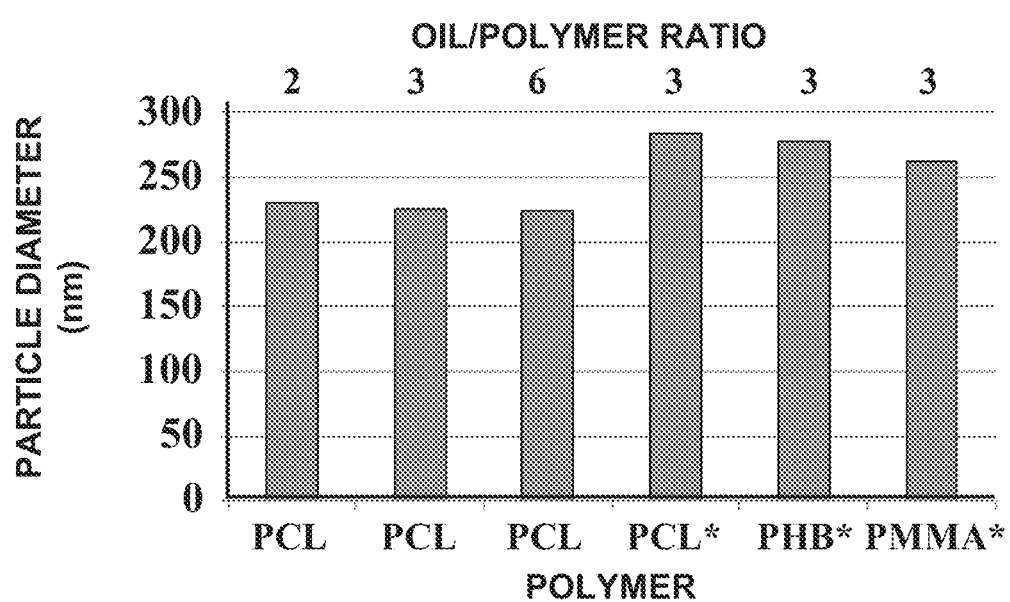

For example, in an experiment in which the Neem oil/amount of polymer ratio was varied with a fixed oil content there is no significant variation in particle diameter. The same result is found by changing the type of polymer (PCL: Poly-ε-caprolactone; PHB: Poly-3-hydroxybutyrate; PMMA: Poly-methyl methacrylate) (FIG. 6).

The adopted strategy mainly attempts to prepare Neem nanoparticles with high azadirachtin content, promoting an increase in dispersion of said limonoid in aqueous medium. For the method by Fessi, H. et al. Nanocapsule formation by interfacial deposition following solvent displacement. *Int. J. Pharm.* 55, R1-R4, 1989, a limit of 75% in encapsulation efficiency was observed.

After preparation of the Neem nanocapsules through the present process and chromatographic analyses following the above procedures in the present specification, colloidal suspensions were obtained with nearly 100% recovery and encapsulation efficiency for the azadirachtin used in the process.

The following Table 4 shows the quantitative characterization of Neem nanocapsules in colloidal suspension obtained through the inventive process.

TABLE 4

| Example | Nominal Concentration* ($\mu g\ mL^{-1}$) | Absolute Recovery (%) | Encapsulation Efficiency (%) |
|---|---|---|---|
| 1 | 80.0 | 101 ± 9.35 | ≥98.0 |
| 2 | 80.0 | 96.7 ± 5.07 | ≥98.0 |
| 3 | 40.0 | 97.6 ± 8.36 | ≥97.5 |
| 4 | 40.0 | 98.1 ± 7.12 | ≥97.5 |

*For the colloidal suspension; Values express average result ± standard deviation (n = 3).

Recovery is determined by CLAE evaluation; first, the amount of azadirachtin present in oil and extracts used in the process is divided by the total content quantified in the resulting colloidal suspension.

For example, the formulation in Example 1, prepared with 4.00 g of a 4,000.0 mg $Kg^{-1}$ enriched oil, must comprise, in the end, 8.00 mg of azadirachtin in a final volume set to 200.0 mL. This quantity amounts to the nominal value of 80.0 $\mu g\ mL^{1}$.

For the formulations described in Table 2, encapsulation efficiency is greater than the quantification limit of the analytical method, that is, approximately 100%.

Encapsulation efficiency of azadirachtin in up to 3.300,0 mg $L^{-1}$ colloidal suspensions (Table 5) was tested by using different amounts of extracts in preparing formulations.

In all Example formulations, absolute recovery and encapsulation efficiency are the same as those listed in Table 4.

Recovery efficiency was calculated after quantification of the colloidal suspensions by CLAE, nominal concentration being the reference value.

Particle diameter, polydispersity index, pH, and zeta potential of such formulations are similar to those described in Table 3.

TABLE 5

| Example | Nominal Concentration* ($\mu g\ mL^{-1}$) | Absolute Recovery (%) | Encapsulation Efficiency (%) |
|---|---|---|---|
| 7 | 2.200.0 | 102.2 ± 1.89 | 98.7 ± 0.01 |
| 8 | 2.800.0 | 99.2 ± 1.03 | 98.8 ± 0.04 |
| 9 | 3.400.0 | 95.8 ± 2.00 | 98.8 ± 0.01 |

*Values express average result ± standard deviation (n = 3).

Azadirachtin solubility has been estimated at 26.0 mg 100 $mL^{-1}$; colloidal suspensions are prepared (40) in aqueous phase with an azadirachtin content of 340.0 mg 100 $mL^{-1}$. This value represents an azadirachtin dispersion capability 13 times greater than its solubility. That is, it is possible to prepare a new formulation for applying Neem extracts and oil with high azadirachtin contents, whereas the surfactant content is kept low (Tween®80=0.5% m/v). It should be clear for those skilled in the art that this value represents a non-limiting example; greater dispersion capabilities are fairly possible according to the extract content used.

Figure 7:
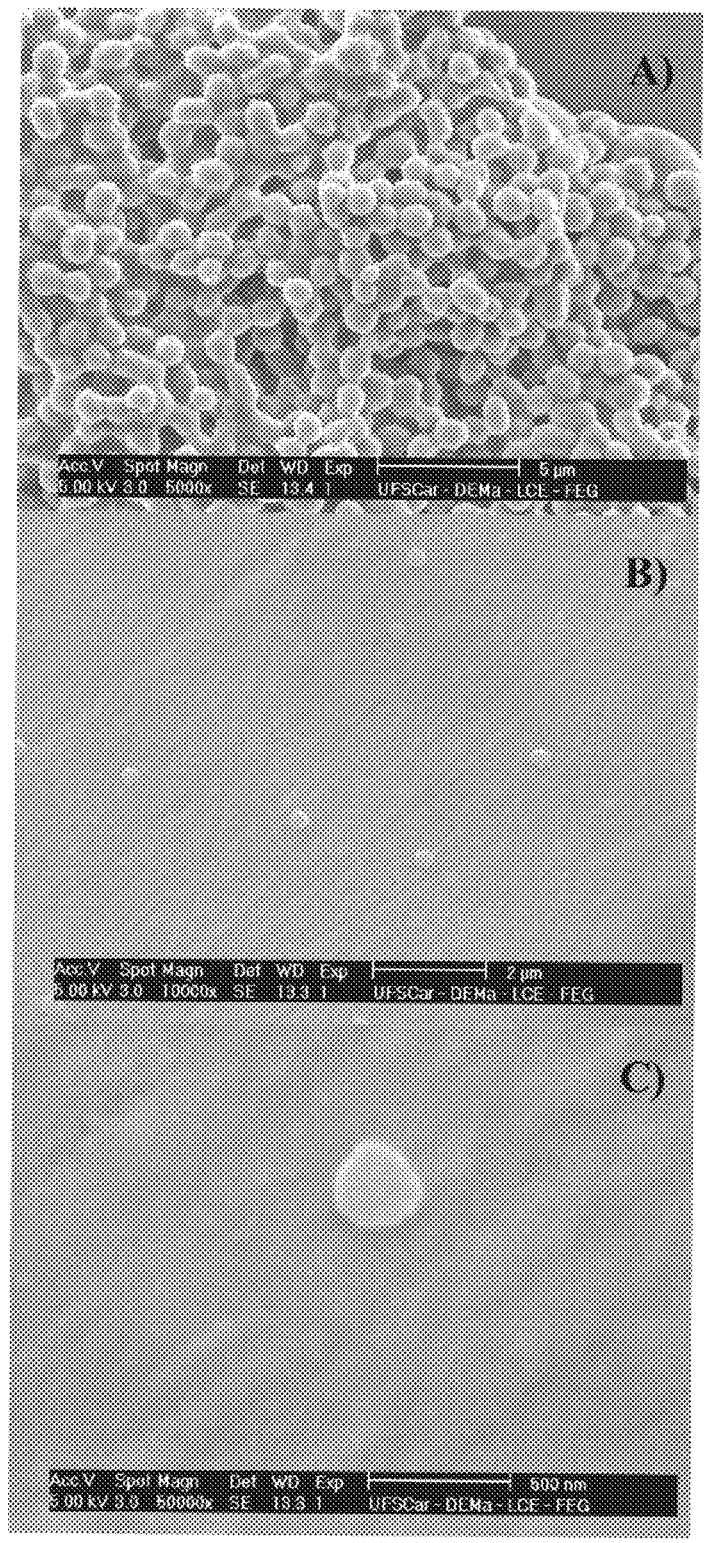

In order to evaluate spherical nanocapsule formation, morphology is determined through scanning electron microscopy (MEV) analysis. Water removal from the colloidal dispersion on the metallic specimen holder, required for preparing samples for MEV morphological analyses, promotes nanoparticle clustering, which forms a polymer film. However, it is possible to observe nanocapsules on the polymer film (FIG. 7).

Nanocapsule Microparticles

Colloidal suspensions generally have limited physical-chemical stability. Long storage periods may promote microbial growth and polymer hydrolysis. Often, out of convenience, turning such liquid systems into powder becomes a viable strategy. Powder nanoparticles may show greater stability, in addition to reducing storage volume and weight for transport.

Indeed, nanoparticles are trapped in a dry solid matrix (powder microparticles) following interaction with silica particles before drying. During the drying process, formation of silica clusters surrounded by one or several Neem nanocapsules covering the microparticle surface is observed; see Pohlmann, A. R. et al. Spray-dried indomethacin-loaded polyester nanocapsules and nanospheres: development, stability evaluation and nanostructure models. *Eur. J. Pharm. Sci.* 16, 305-312, 2002.

This process can avoid irreversible nanocapsule clustering; see Tewa-Tagne, P. et al. Spray-dried microparticles containing polymeric nanocapsules: formulation aspects, liquid phase interaction and particles characteristics. *Int. J. Pharm.* 325, 63-74, 2006.

Colloidal silicon dioxide was proven a good drying excipient candidate. Among the advantages, colloidal silicon may yield a great surface area and have good thermal conductivity, which facilitates water removal. Additionally, it is a non-toxic biocompatible material, considered safe even for manufacturing drugs.

In developing the drying process, nanocapsules with particle diameter lower than 300 nm are used, having negative charges relative to zeta potential (~-30 mV).

As proposed by Pohlmann, A. R. in the abovementioned article in this specification, and in the article by Tewa-Tagne, P. also mentioned above in the present specification, yield was evaluated by the percentage of silica (Aerosil®200) used in the drying process by Spray-Dryer.

During preparation of powder microparticles (60) through nanocapsule combination (50) with drying excipient (e.g. silica) in Spray-Dryer, nanocapsule/silica ratios range from 1:0.2 to 1:2 m/m.

Data is gathered in Table 6 below.

TABLE 6

| | Content at Preparation % (m/v) | | |
|---|---|---|---|
| Samples | Nanocapsules | Silica | Yield (%) |
| 10 | 1.0 | 0.5 | 72.1 ± 1.9 |
| 11 | 1.0 | 1.0 | 78.9 ± 2.2 |
| 12 | 1.0 | 1.5 | 80.5 ± 1.3 |
| 13 | 1.0 | 2.0 | 78.7 ± 1.5 |
| 14 | 2.0 | 1.0 | 52.3 ± 4.6 |
| 15[a] | 2.0 | 1.0 | 39.1 ± 6.9 |

[a]Formulation without Span ® 60.
*Values express average result ± standard deviation (n = 3).

For different formulations used in feeding the Spray-Dryer with 1.0% nanocapsule, he best yields were obtained for a silica quantity greater than 1.0%. Below such composition, formation of a film was observed on the cyclone walls due to adsorption of the nanocapsule material and silica (Sample 10). The same profile was observed with the increase in the amount of nanocapsules relative to the amount of silica (Sample 14).

The worst recovery results were obtained for nanoparticles prepared without the surfactant Span®60 (Sample 15) leading to strong adsorption on the cyclone walls.

The data in Table 6 show the importance of controlling component quantities subject to the drying process by Spray-Dryer.

Particle recovery in Neem/silica microparticle powder showed an acceptable yield for the Spray-Drying process.

Operational parameters for the Spray-Dryer equipment, including feed rate, atomizing air flow, aspirator capacity, and input temperature, were such that allowed for obtaining an output temperature of 50±5° C., favorable to not thermally decomposing sensitive compounds such as azadirachtin.

Figure 8:
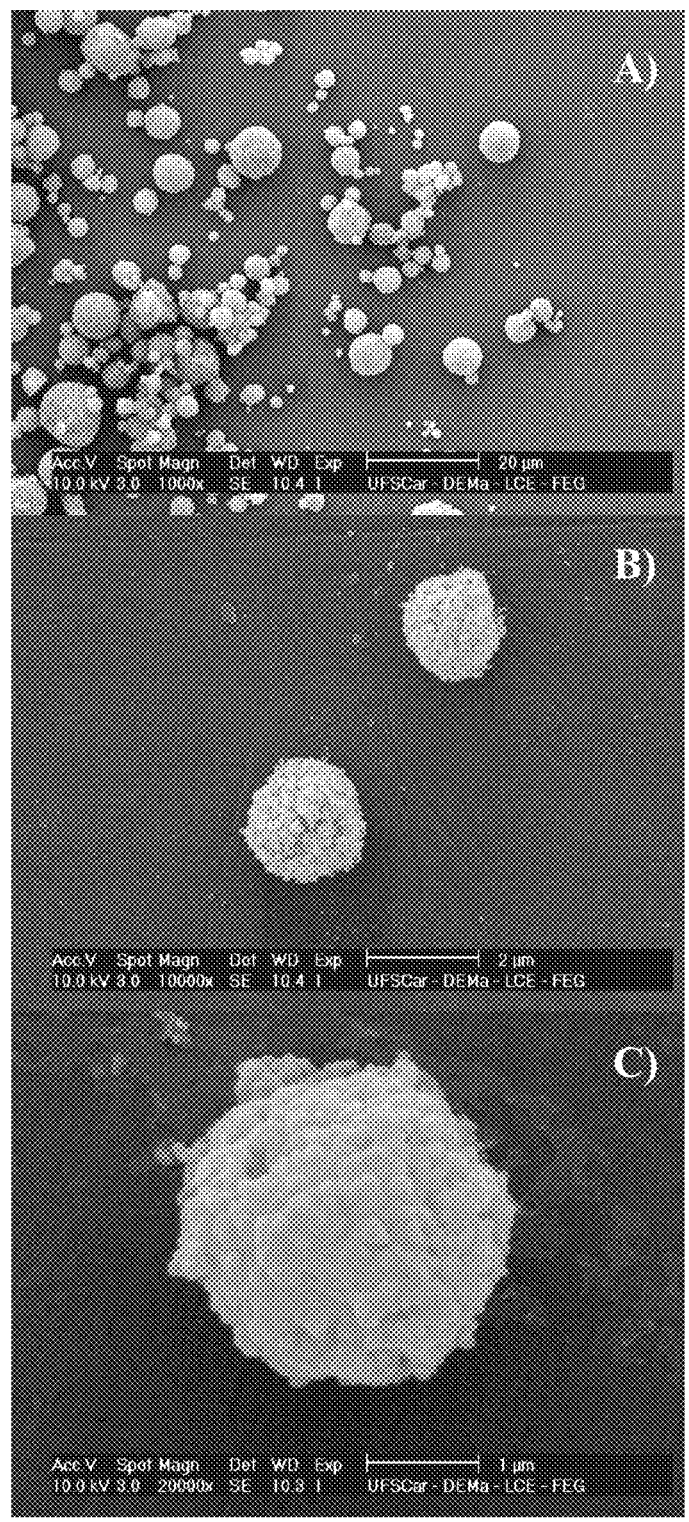

Neem nanocapsule powder microparticle form and morphology obtained in the Spray-Drying drying process can be observed in FIG. 8.

Well separated spherical powder microparticles were obtained with various diameters ranging from 1 to 10 μm. The spherical shape infers absence of destabilizing effects during the drying process.

Nanocapsules were observed over the powder microparticles showing reduced average diameter (<100 nm) through MEV analysis with high magnifications (FIG. 8c).

The same behavior was observed and described by Pohlmann, A. R. in the abovementioned article in the present specification.

Particle surfaces had a rough aspect with a porous nanoparticle and silica layer. Even though preparations are homogenous, particle diameter dispersion derives from the atomization system tip, which produces drops with a wide size range. Thus, different drop sizes lead to a wide particle diameter dispersion.

Particle fusion in the final drying step can also afford greater clusters.

Quantitative analysis of the azadirachtin content by CLAE was carried out as above described in the present specification.

Formulations which are prepared with different azadirachtin amounts in Neem enriched oils and extracts led to the preparation of powder microparticles with varied azadirachtin contents proportional to the formulation's total mass.

Final azadirachtin content in the powder microparticles varied from 1,600.0 mg Kg$^{-1}$ to 6,800.0 mg Kg$^{-1}$. However, such result only illustrates the values of some experiments; the amount of azadirachtin can greatly vary depending on the azadirachtin content in Neem oil and extracts, and on the quantity thereof which is applied in the formulation. In a non-limiting example, it is possible to prepare powder microparticles with contents of 10,000 mg Kg$^{-1}$, depending on quantity and quality of the Neem extract used.

Evaluation of polymer-Neem product interaction was carried out by thermogravimetry (TG) and derivative thermogravimetry (DTG). In this study, the physical-chemical interaction among formulation constituents was analyzed so as to predict thermal and biodegradable behavior of particles. Mass loss was between 45 and 50%, proportional to the composition of the formulations and to the amount of silica used.

The evaluated formulations are listed in Table 7.

TABLE 7

| Formulation | Polymer (PCL) | Neem Extract | Neem Oil | Span ® 66 | Tween ® 80 |
|---|---|---|---|---|---|
| A | Yes | No | No [a] | Yes | Yes |
| B | Yes | No | Yes | Yes | Yes |
| C | Yes | Yes | Yes | Yes | Yes |
| D | Ne | Yes | No | Yes | Yes |
| E | Ne | No | No [a] | Yes | Yes |

[a] In this composition, isodecyl oleate was used.

It was clearly possible to identify different thermal events for mass losses due to the material present. Because of the substitution of Neem oil for isodecyl oleate, the formulations did not necessarily present the same thermal events. However, important observations can be put forth.

Figure 9A:
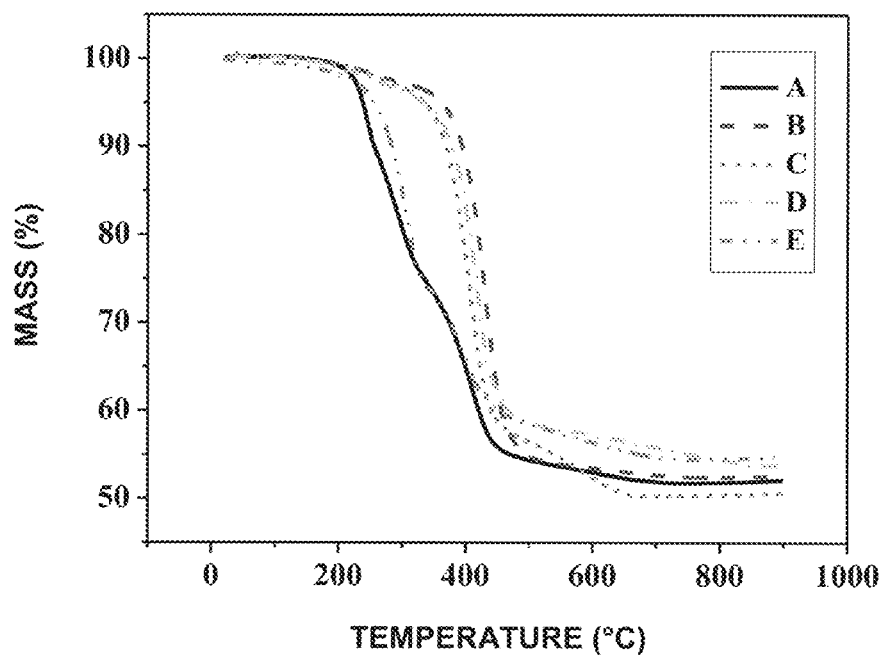
Figure 9B:
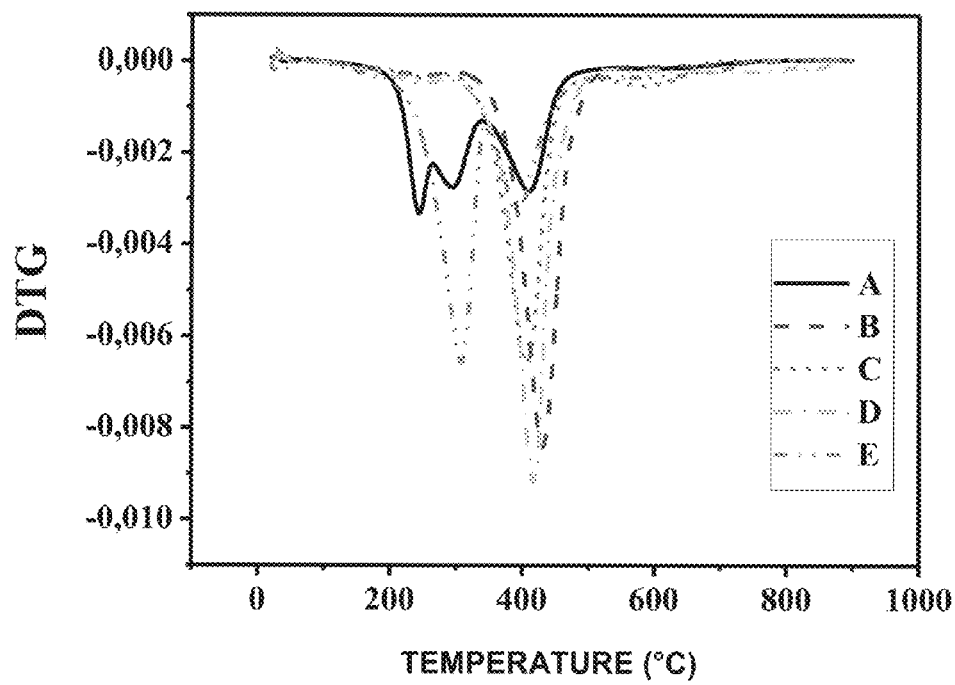

Formulations A to E comprising Neem oils and extracts exhibited a late degradation curve when compared to formulations without Neem extracts and/or oil (FIG. 9A—TG curve, FIG. 9B, DTG curve). This is justified by the first thermal event resulting from the decomposition of Neem extracts and/or oils used in the formulation. The second event occurs by Span®60 and Tween®80 degradation. When comparing the PCL formulation to Neem oil (B—Table 7 above) e PCL to isodecyl oleate (B—Table 7 above), it can be observed that Neem oil delays Span®60 and Tween®80 degradation. The last event occurs because of polymer degradation. After said events, material decomposition occurs slowly, probably due to elimination of carbonated materials.

Nanoparticle Stability

Nanoparticle stability in colloidal suspension and in powder microparticles subject to Ultraviolet radiation is reported with respect to remaining azadirachtin percentage (FIG. 10).

Two non-encapsulated Neem oil samples are used as reference standards, one being exposed to ultraviolet radiation (E—FIG. 10) and the other being housed away from ultraviolet radiation (F—FIG. 10). For the evaluation period, samples were continuously homogenized.

Degradation rate of the Neem oil sample exposed to ultraviolet radiation was far higher when compared to nanoencapsulated samples.

The oil sample which was housed away from ultraviolet radiation did not bear photodegradation signs during the investigative period.

Different ultraviolet degradation rates were also observed among powder nanoparticles (A and B—FIG. 10) and in colloidal suspension (C and D—FIG. 10).

Degradation rate of nanocapsules in colloidal suspension was higher than that of powder nanocapsules. This difference can be explained by polymer swelling and azadirachtin release in aqueous medium, and by the ability of silica nanoparticles to absorb or reflect ultraviolet radiation. Moreover, there is less ultraviolet penetration in the powder. Samples comprising Span®60 (B and D—FIG. 10) show lower photodegradation than samples without Span®60 (A and C—FIG. 10).

When samples were radiated for 7 days, the photodegraded azadirachtin content in the exposed oil was approximately 100%, while in powder nanoparticles and in colloidal suspension it was 90% and 55% respectively. After 14 days, the photodegraded azadirachtin content in powder nanoparticles and in colloidal suspension was 25% and 72% respectively.

Azadirachtin photodegradation constant values (days$^{-1}$) are described in Table 8 bellow in the present specification.

The difference among the photodegradation constant values confirms that azadirachtin was encapsulated and partially protected, mainly in solid matrices. One objective of the present investigation was to determine the photodegradation efficiency required to reduce the azadirachtin content to 50% of the initial value under accelerated conditions for encapsulated and non-encapsulated azadirachtin samples (Table 8).

From the data in Table 8, the difference in ultraviolet stability among samples becomes evident, powder nanoparticles being more stable than those in colloidal suspension.

As expected, non-encapsulated oil offers the best photoprotection for azadirachtin.

TABLE 8

| Samples | Photodegradation Constants$^a$ (k, days$^{-1}$) | Photodegradation Efficiency$^b$ (days) |
|---|---|---|
| Neem Oil Exposed to UV Radiation | 0.50010 | 1.39 |
| Neem Oil Protected from UV Radiation | 0.00110 | 630 |
| A-Powder NP (without Span ® 60) | 0.02014 | 34.4 |
| B-Powder NP (with Span ® 60) | 0.01271 | 54.5 |
| C-NP in Colloidal Suspension (without Span ® 60) | 0.09923 | 6.98 |
| D-NP in Colloidal Suspension (with Span ® 60) | 0.08902 | 7.78 |

$^a$First-order kinetics constants: In[Aza]$_t$/[Aza]$_0$ = − kt
$^b$Radiation time required (in days) so as to reduce the azadirachtin content in 50% of its initial value.

Release Study of Azadirachtin from PCL Nanocapsules

Release kinetics was investigated for nanocapsules with higher ultraviolet stability, i.e., nanocapsules formulated with Span®60. The system designed upon constant flow avoids system saturation, and, accordingly, solubility equilibrium. In this essay, only non-encapsulated azadirachtin is capable of passing through dialysis tubing pores.

In vitro release profile can be observed in FIG. 11. The required time for 100% azadirachtin release was 10 hours, 85% being released within the first four hours.

The value of n is an empirical parameter obtained by Korsmeyer's Equation, R. W. et al. Mechanisms of solute release from porous hydrophilic polymers. *Int. J. Pharm.* 15, 25-35, 1983, used for characterizing the release mechanism based on the following equation:

$$M_t/M_\infty = K \cdot t^n$$

where $M_t/M_\infty$ is the release fraction at time t, n is the release exponent and K is the release factor.

According to the numerical value assumed by n, it is possible to characterize the drug's release system. This semi-empirical equation is used for describing solute release (azadirachtin). In this case, for n≤0.45 values, the main mechanism which controls azadirachtin release is pure diffusion (Fickian classic).

When n assumes values between 0.45<n≤0.89, it is indicative of aberrant transportation kinetics, that is, a combination of drug diffusion mechanisms (Fickian transport) and non-Fickian transport (Case-II), controlled by polymer chain relaxation.

The value of n determined by the slope coefficient of the log($M_t/M_\infty$) versus log(t) plot for azadirachtin was 2.49 (>0.89), which corresponds to first-order kinetics, release being controlled by transport mechanisms derived from polymer swelling and relaxation phenomena, or release upon erosion.

Results indicate that PCL nanocapsules comprising Neem oil and extracts in colloidal suspension are appropriately prepared by the provided method.

Neem powder nanocapsules can be easily prepared by drying the colloidal suspensions by Spray-Dryer.

Products exhibit good homogeneity and stability in colloidal suspension and powder. The association rate (encapsulation efficiency), monitored by azadirachtin, was close to 100%, the in vitro release profile being stipulated by the zero-order kinetics, that is, ruled by polymer swelling and relaxation.

Azadirachtin recovery, determined in colloidal suspensions, was 100%, which proves that there was no compound loss during preparation.

Products obtained by the inventive process show an increase in stability against ultraviolet radiation compared to commercially available Neem oil products.

The use of Neem oil enriched with Neem extracts allowed for obtaining products with desired and reproducible azadirachtin contents.

The developed and validated High Performance Liquid Chromatography analytical technique was efficient in quantitative azadirachtin control in extracts, oils, and nanoparticles, such control being necessary for preparing and characterizing the nanoparticles.

The invention claimed is:

1. A process for obtaining biopolymeric nanoparticles containing *Azadirachta indica* A. Juss. (Neem) oil comprising the steps of:
    (a) separately forming (i) an aqueous phase comprising a nanoemulsion comprising Neem oil and water; and (ii) an organic phase comprising a biopolymer solution comprising a biopolymer dissolved in a water miscible organic solvent, wherein the biopolymer is dissolvable in acetone;
    (b) mixing the organic phase with the aqueous phase by slowly adding the organic phase to the aqueous phase with stirring so that the organic solvent diffuses into the aqueous phase and the polymer is deposited at an oil-water interface to form a biopolymeric nanoparticle colloidal dispersion; and then either (c1) directly forming the colloidal dispersion into nanoparticles by reducing a volume of the water and solvent in the colloidal dispersion to form the biopolymeric nanoparticles; or (c2) mixing the colloidal dispersion with a second aqueous phase comprising a non-ionic surfactant to stabilize the colloidal dispersion and then reducing a volume of the water and solvent in the colloidal dispersion to form the biopolymeric nanoparticles.

2. The process according to claim 1, comprising the step (c2) of mixing the colloidal dispersion with a second aqueous phase comprising a non-ionic surfactant to stabilize the colloidal dispersion and then reducing a volume of the water and solvent in the colloidal dispersion to form the biopolymeric nanoparticles.

3. The process according to claim 1, wherein the nanoemulsion comprises a first non-ionic surfactant.

4. The process according to claim 3, wherein the first non-ionic surfactant is a sorbitan monostearate.

5. The process according to claim 1, comprising the step (c1) of directly forming the colloidal dispersion into nanoparticles by reducing a volume of the water and solvent to form the biopolymeric nanoparticles.

6. The process according to claim 2, wherein the non-ionic surfactant is a polyethoxysorbitan.

7. The process according to claim 2, wherein the Neem oil in the nanoemulsion is formed by macerating Neem seed kernels to an average particle diameter between 10 and 30 µm, and solvent extraction of the Neem oil from the macerated Neem seed kernels.

8. The process according to claim 7, wherein the nanoemulsion is formed in step (a) by mixing from 0.5 to 10% (m/v) of Neem oil, from 0.1 to 5% (m/v) of a Neem extract for enriching a content of azadirachtin in the Neem oil, and from 0.1 to 2% (m/v) of the non-ionic surfactant, wherein the Neem extract is an ethanol extract of a product remaining after solvent extraction of the Neem oil from the Neem seed kernels.

9. The process according to claim 6, wherein the aqueous phase contains from 0.1 to 2% (m/v) of the non-ionic surfactant.

10. The process according to claim 2, comprising adjusting a final volume of the nanoparticles in the stabilized dispersion by removing solvent and part of the water remaining by vacuum, and recovering the biopolymeric nanoparticles.

11. The process according to claim 1, wherein the water miscible organic solvent is selected from the group consisting of acetone and a mixture of acetone and ethanol.

12. The process according to claim 1, wherein the biopolymer does not comprise an alginate.

13. A process for obtaining biopolymeric nanoparticles containing *Azadirachta indica* A. Juss. (Neem) oil comprising the steps of:

(a) separately forming (i) a nanoemulsion comprising Neem oil and water; and (ii) a biopolymer solution comprising a biopolymer dissolved in a water miscible organic solvent;

(b) mixing the nanoemulsion with the biopolymer solution by slowly adding the biopolymer solution to the nanoemulsion with stirring to form a biopolymeric nanoparticle colloidal suspension, wherein the mixing step (b) comprises dissolving under stirring and heating at 40° C.-50° C. from 0.1 to 2.0% (m/v) biopolymer in the water miscible organic solvent and slowly pouring, by means of a peristaltic pump, the biopolymer solution onto the nanoemulsion with stirring to cause deposition of the biopolymer on an oil-water interface to form the biopolymeric nanoparticle colloidal suspensions with a pH between 4.0 and 7.0.

14. A process for obtaining biopolymeric nanoparticles containing *Azadirachta indica* A. Juss. (Neem) oil comprising the steps of:

(a) separately forming (i) a nanoemulsion comprising Neem oil and water; and (ii) a biopolymer solution comprising a biopolymer dissolved in a water miscible organic solvent; and (b) mixing the nanoemulsion with the biopolymer solution by slowly adding the biopolymer solution to the nanoemulsion with stirring to form a biopolymeric nanoparticle colloidal suspension, wherein the biopolymer is a polyester selected from the group consisting of lactide and glycolide homo- and copolymers (PLA, PGA, PLGA), poly-ϵ-caprolactone (PCL), and poly (beta-hydroxy-butyric acid) (PHB).

15. The process according to claim 14, wherein the biopolymer is PCL.

* * * * *